(12) United States Patent
Adam-Worrall et al.

(10) Patent No.: US 7,700,634 B2
(45) Date of Patent: Apr. 20, 2010

(54) (INDOL-3-YL) HETEROCYCLE DERIVATIVES AS AGONISTS OF THE CANNABINOID CB1 RECEPTOR

(75) Inventors: Julia Adam-Worrall, Newhouse (GB); Angus John Morrison, Newhouse (GB); Grant Wishart, Newhouse (GB); Takao Kiyoi, Newhouse (GB); Duncan Robert McArthur, Newhouse (GB)

(73) Assignee: N.V. Organon, Oss (NL)

( * ) Notice: Subject to any disclaimer, the term of this patent is extended or adjusted under 35 U.S.C. 154(b) by 0 days.

(21) Appl. No.: 10/590,674

(22) PCT Filed: Feb. 28, 2005

(86) PCT No.: PCT/EP2005/050833
§ 371 (c)(1),
(2), (4) Date: Aug. 26, 2006

(87) PCT Pub. No.: WO2005/089754
PCT Pub. Date: Sep. 29, 2005

(65) Prior Publication Data
US 2007/0142446 A1    Jun. 21, 2007

Related U.S. Application Data

(60) Provisional application No. 60/550,563, filed on Mar. 5, 2004.

(30) Foreign Application Priority Data
Mar. 5, 2004  (EP) .................. 04100902
Aug. 12, 2004  (EP) .................. 04103901

(51) Int. Cl.
*A01N 43/82* (2006.01)
*A01N 43/78* (2006.01)
*C07D 285/08* (2006.01)
*C07D 271/06* (2006.01)
*C07D 277/04* (2006.01)

(52) U.S. Cl. ................ 514/363; 514/364; 514/365; 548/128; 548/131; 548/146

(58) Field of Classification Search ................ None
See application file for complete search history.

(56) References Cited

U.S. PATENT DOCUMENTS

| | | | |
|---|---|---|---|
| 4,939,138 A | 7/1990 | D'Ambra et al. ............ 514/218 |
| 2007/0082931 A1 | 4/2007 | Ratcliffe et al. | |
| 2007/0142446 A1 | 6/2007 | Adam-Worrall et al. | |

FOREIGN PATENT DOCUMENTS

| WO | WO 01/58869 A2 | 8/2001 |
|---|---|---|
| WO | WO 01/58869 A3 | 8/2001 |
| WO | WO 02/36590 A1 | 5/2002 |
| WO | WO 02/060447 A1 | 8/2002 |
| WO | WO 2004/000832 A1 | 12/2003 |
| WO | WO 2005/058327 A1 | 6/2005 |
| WO | WO 2005/089754 A1 | 9/2005 |
| WO | WO 2007/023143 A1 | 3/2007 |
| WO | WO 2008/101995 A1 | 8/2008 |

OTHER PUBLICATIONS

Hacks Chemical Dictionary, Fourth Edition, Julius Grant, 1972, p. 203.*
/ Huffman et al., "structure-activity relationship for 1-alkyl-3-(1-naphthoyl)indoles at the cannabinoid CB1 and CB2 receptors: steric and electronic effects of naphthoyl substituents. New highly selective CB2 receptor agonists", bioorganic&medicinal chemistry, 13, 2005, 89-112.*
/ Tarzia et al., "Synthesis and structure-activity relationships of a series of pyrrole cannabinoid receptor agonists", bioorganic&medicinal chemistry 2003, 11, 3965-3973.*
International Search Report for Application No. PCT/EP2005/050833 dated Jun. 21, 2005.
International Preliminary Examination Report on Patentability of International Application No. PCT/EP2005/050833 dated Jan. 31, 2006.
Written Opinion of International Application No. PCT/EP2005/050833 dated Jun. 21, 2006.
Howlett, A. C. et al., "International Union of Pharmacology. XXVII. Classification of Cannabinoid Receptors," Pharmacological Reviews, vol. 54, No. 2 (2002) pp. 161-202.
Iversen, L. et al., "Cannabinoids: a real prospect for pain relief?," Current Opinion in Pharmacology, vol. 2 (2002) pp. 50-55.
Eissenstat, M. A. et al., "Aminoalkylindoles: Structure-Activity Relationships of Novel Cannabinoid Mimetics," J. Med. Chem., vol. 38 (1995), pp. 3094-3105.

(Continued)

*Primary Examiner*—Golam M. M. Shameem
*Assistant Examiner*—Sun Jae Y Loewe
(74) *Attorney, Agent, or Firm*—Susan Hess

(57) ABSTRACT

Disclosed herein are indole derivatives of the formula (I)

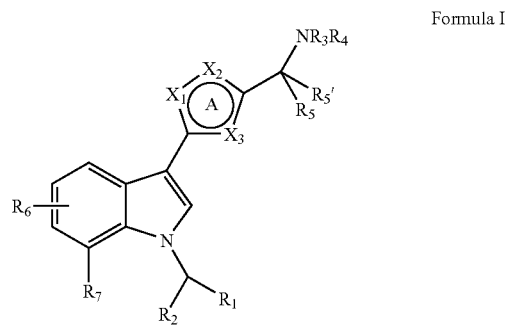

Formula I wherein each of the substitutents is given the definition as set forth in the specification and claims. Also disclosed are pharmaceutical compositions containing the indole derivatives and use of the derivatives for the treatment of pain.

14 Claims, No Drawings

OTHER PUBLICATIONS

Adam. J. et al., "Recent advances in the cannabinoids," Expert Opin. Ther. Patents, vol. 12 (2002) pp. 1475-1489.

van Wijngaarden, I. et al., "Development of High-Affinity 5-$HT_3$ Receptor Antagonists. Structure-Affinity Relationships of Novel 1,7-Annelated Indole Derivatives," J. Med. Chem., vol. 36 (1993) pp. 3693-3699.

Hwu, J. R. et al., "Novel Methods for the Synthesis of Functionalized Indoles from Arylhydroxylamines and Activated Acetylenes," J. Org. Chem., vol. 59 (1994) pp. 1577-1582.

Robinson, B., "Recent Studies on the Fischer Indole Synthesis," Chem. Rev., vol. 63 (1963) pp. 227-250.

Miyaura, N. et al., "Palladium-Catalyzed Cross-Coupling Reactions of Organoboron Compounds," Chem. Rev., vol. 95 (1995) pp. 2457-2483.

Stratowa, C. et al., "Use of a luciferase reporter system for characterizing G-protein-linked receptors," Current Opinion in Biotechnology, vol. 6 (1995) pp. 574-581.

Luly, J. R. et al., "A Synthesis of Protected Aminoalkyl Epoxides from a-Amino Acids," J. Org. Chem., vol. 52 (1987) pp. 1487-1492.

Jutz, C., "The Vilsmeier-Haack-Arnold Acylations. C-C Bond-Forming Reactions of Chloromethyleniminium Ions," Adv. Org. Chem., vol. 9, Part I (1976) pp. 252-342.

International Search Report dated Nov. 13, 2006 for International Application No. PCT/EP2006/065496 and Written Opinion dated Nov. 13, 2006 for International Application No. PCT/EP2006/065496.

Yaksh, T. et al., "An automated flinch detecting system for use in the formalin nociceptive bioassay", *J. Appl. Physiol.* 90:2386-2402 (2001).

PCT International Search Report dated Apr. 23, 2008 and Written Opinion dated Apr. 23, 2008 for related International Application No. PCT/EP2008/052141.

\* cited by examiner

(INDOL-3-YL) HETEROCYCLE DERIVATIVES AS AGONISTS OF THE CANNABINOID CB1 RECEPTOR

The present invention relates to (indol-3-yl)-heterocycle derivatives, to pharmaceutical compositions comprising the same and to the use of these (indol-3-yl)-heterocycle derivatives in therapy, especially in the treatment of pain.

Pain treatment is often limited by the side effects of currently available medication. For moderate to severe pain, opioids are widely used. These agents are cheap and effective but suffer from serious and potentially life-threatening side effects, most notably respiratory depression and muscle rigidity. In addition, the doses of opioids which can be administered are limited by nausea, emesis, constipation, pruritis and urinary retention, often resulting in patients electing to receive sub-optimal pain control rather than suffer these distressing side effects. Furthermore, these side effects often result in patients requiring extended hospitalisation. Opioids are highly addictive and are scheduled drugs in many territories. There is therefore a demand for new analgesics that have an improved side effect profile compared to currently used products, at equi-analgesic doses.

Evidence is accumulating that cannabinoid agonists have potential as analgesic and anti-inflammatory agents. Two types of cannabinoid receptors are implicated, the cannabinoid CB1 receptor, which is located primarily in the central nervous system but which is also expressed by peripheral neurones and to a lower extent in other peripheral tissues, and the cannabinoid CB2 receptor, which is mostly located in immune cells (Howlett, A. C. et al.: International Union of Pharmacology. XXVII. Classification of Cannabinoid Receptors. *Pharmacol. Rev.* 54, 161-202, 2002). While the CB2 receptor has been implicated in modulating the immune and anti-inflammatory response of cannabinoids, cannabinoid receptor agonists, especially those acting at the CB1 receptor have been suggested as useful in the treatment of pain (see Iversen, L. and Chapman, V. *Current Opinion in Pharmacology*, 2, 50-55, 2002 and references therein).

WIN 55,212-2, the mesylate salt of (R)-(+)-[2,3-dihydro-5-methyl-[(morpholinyl) methyl]pyrrolo[1,2,3-de]-1,4-benzoxazinyl]-(1-naphthalenyl)methanone was disclosed in U.S. Pat. No. 4,939,138 (Sterling Drug Inc.) as an analgesic agent. The compound is the prototype of aminoalkylindoles (Eissenstat, M. A. et al., *J. Med. Chem.* 38, 3094-3105, 1995), which are potent cannabinoid CB1 receptor agonists that can produce antinociception with equivalent efficacy to morphine in animal models of acute pain, persistent inflammatory pain and neuropathic pain.

Key structural features of aminoalkylindoles having cannabimimetic properties (Adam, J. and Cowley, P. *Expert Opin. Ther. Patents*, 12, 1475-1489, 2002) are an aminoalkyl substituent at the 1-position of the indole moiety, and a further bulky substituent in the 3-position of the indole ring, such as exemplified by an aroyl group in the aminoalkylindoles disclosed in U.S. Pat. No. 4,939,138 (Sterling Drug Inc.) and in the more recent WO02060447 ((University of Connecticut), or by a substituted amido-group in the compounds disclosed in WO0158869 (Bristol-Myers Squibb). Recently, 1-(aminoalkyl)indole derivatives having a substituted oxadiazol-5-yl ring at the 3-position were disclosed in WO0236590 (Amrad Operations PTY Ltd.) as cannabinoid receptor modulators and useful as analgesic agents.

There remains a need for cannabinoid agonists with improved properties, such as increased water solubility, for use as therapeutic agents.

To this end the present invention provides (indol-3-yl)-heterocycle derivatives having the general Formula I

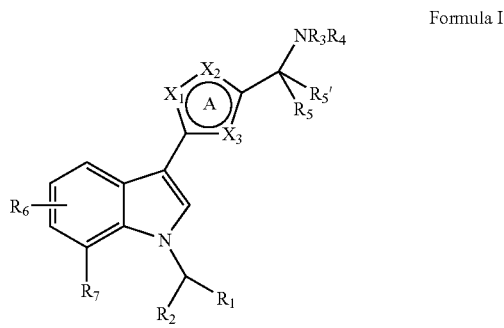

Formula I wherein

A represents a 5-membered aromatic heterocyclic ring, wherein $X_1$, $X_2$ and $X_3$ are independently selected from N, O, S and CR;

R is H or $(C_{1-4})$alkyl; or

R, when present in $X_2$ or $X_3$, may form together with $R_3$ a 5-8 membered ring;

$R_1$ is a 5 to 8-membered saturated carbocyclic ring, optionally containing a heteroatom selected from O and S;

$R_2$ is H, $CH_3$ or $CH_2$—$CH_3$; or $R_2$ is joined together with $R_7$ to form a 6-membered ring, optionally containing a heteroatom selected from O and S, and which heteroatom is bonded to the 7-position of the indole ring;

$R_3$ and $R_4$ are independently H, $(C_{1-6})$alkyl or $(C_{3-7})$cycloalkyl, the alkyl groups being optionally substituted with OH, $(C_{1-4})$alkyloxy, $(C_{1-4})$alkylthio, $(C_{1-4})$alkylsulfonyl, CN or halogen; or $R_3$ together with $R_4$ and the N to which they are bonded form a 4-8 membered ring optionally containing a further heteroatom selected from O and S, and which is optionally substituted with OH, $(C_{1-4})$alkyl, $(C_{1-4})$alkyloxy, $(C_{1-4})$alkyloxy-$(C_{1-4})$alkyl, or halogen; or $R_3$ together with $R_5$ forms a 4-8 membered ring optionally containing a further heteroatom selected from O and S, and which is optionally substituted with OH, $(C_{1-4})$alkyl, $(C_{1-4})$alkyloxy, $(C_{1-4})$alkyloxy-$(C_{1-4})$alkyl, or halogen; or $R_3$ together with R, when present in $X_2$ or $X_3$, forms a 5-8 membered ring;

$R_5$ is H or $(C_{1-4})$alkyl; or $R_5$ together with $R_3$ forms a 4-8 membered ring optionally containing a further heteroatom selected from O and S, and which is optionally substituted with OH, $(C_{1-4})$alkyl, $(C_{1-4})$alkyloxy, $(C_{1-4})$alkyloxy-$(C_{1-4})$alkyl, or halogen;

$R_5'$ is H or $(C_{1-4})$alkyl;

$R_6$ represents 1-3 substituents independently selected from H, $(C_{1-4})$alkyl, $(C_{1-4})$-alkyloxy, CN and halogen;

$R_7$ is H, $(C_{1-4})$alkyl, $(C_{1-4})$alkyloxy, CN or halogen; or $R_7$ is joined together with $R_2$ to form a 6-membered ring, optionally containing a further heteroatom selected from O and S, and which heteroatom is bonded to the 7-position of the indole ring; or a pharmaceutically acceptable salt thereof, as agonists of the cannabinoid CB1 receptor, which can be used in the treatment of pain such as for example peri-operative pain, chronic pain, neuropathic pain, cancer pain and pain and spasticity associated with multiple sclerosis.

The heterocycle A, as used in the definition of Formula I, represents a 5-membered aromatic heterocyclic ring, which contains 1-3 heteroatoms selected from N, O and S. This means that at least one of $X_1$, $X_2$ and $X_3$, used to define heterocycle A, cannot be CR. Representative heterocycles A are those derived from thiophene, furan, triazole, thiazole, thiadiazole, oxazole, oxadiazole and their isomers including isothiazole, isothiadiazole, isoxazole and isoxadiazole. Preferred heterocycles A are 1,2,4-oxadiazole ($X_1$ is N, $X_2$ is O, $X_3$ is N), 1,2,4-thiadiazole ($X_1$ is N, $X_2$ is S, $X_3$ is N) and thiazole ($X_1$ is S, $X_2$ is CR, $X_3$ is N).

In the definition of Formula I R, when present in $X_2$ or $X_3$, may form together with $R_3$ a 5-8 membered ring, so as to form together with ring A a bicyclic ring system comprising a 5-8 membered N-containing ring which is fused to the 5-membered aromatic heterocyclic ring A. Examples of such fused ring systems are those derived from 5,6-dihydro-4H-pyrrolo[3,4-d]isoxazole, 4,5,6,7-tetrahydro-oxazolo[5,4-c]pyridine, 4,5,6,7-tetrahydro-thiazolo[5,4-c]pyridine, 5,6,7,8-tetrahydro-4H-isoxazolo[5,4-c]azepine, 5,6-dihydro-4H-pyrrolo[3,4-d]thiazole and 5,6-dihydro-4H-pyrrolo[3,4-d]isothiazole.

The term $(C_{1-4})$alkyl as used in the definition of Formula I means a branched or unbranched alkyl group having 1-4 carbon atoms, like butyl, isobutyl, tertiary butyl, propyl, isopropyl, ethyl and methyl.

In the term $(C_{1-4})$alkyloxy, $(C_{1-4})$alkyl has the meaning as defined above.

The term halogen means F, Cl, Br or I.

The term 5-8 membered saturated carbocyclic ring, as used in the definition of $R_1$ of Formula 1, represents a cyclopentyl, a cyclohexyl, a cycloheptyl or a cyclooctyl ring. Such rings may contain a heteroatom selected from O and S to form a saturated heterocyclic ring, such as tetrahydropyranyl, tetrahydrofuranyl, tetrahydrothiopyranyl or tetrahydrothienyl. Preferred carbocyclic rings are cyclohexyl and tetrahydropyranyl.

In the definition of Formula I $R_2$ can be joined together with $R_7$ to form a 6-membered ring, optionally containing a heteroatom selected from O and S, which atom is bonded to the 7-position of the indole ring. In these (indol-3-yl)-substituted 5-membered heterocycles of the invention the indol-3-yl group is part of a tricyclic fused ring system, i.e. a 2,3-dihydro-pyrrolo[3,2,1-ij]quinoline system ($R_7$ and $R_2$ together represent —$CH_2$—$CH_2$—), a 2,3-dihydro-pyrrolo-[1,2,3-de]-1,4-benzoxazine system ($R_7$ and $R_2$ together represent —O—$CH_2$—), or a 2,3-dihydro-pyrrolo[1,2,3-de]-1,4-benzothiazine system ($R_7$ and $R_2$ together represent —S—$CH_2$—). In the definition of Formula I $R_3$ together with $R_4$ and the N to which they are bonded may form a 4-8 membered ring, optionally containing a further heteroatom selected from O and S. Examples of such ring are pyrrolidin-1-yl, piperidin-1-yl, azepin-1-yl, morpholin-4-yl and thiomorpholin-4-yl. Preferred are pyrrolidin-1-yl, piperidin-1-yl and morpholin-4-yl.

In the definition of Formula I $R_3$ together with $R_5$ may form a 4-8 membered ring optionally containing a further heteroatom selected from O and S. It is understood that the N to which $R_3$ is bonded and the carbon atom to which $R_5$ is bonded are part of the 4-8 membered ring. Examples of such rings are pyrrolidin-2-yl, piperidin-2-yl, azepin-2-yl, morpholin-3-yl and thiomorpholin-3-yl.

There is a preference for (indol-3-yl)-heterocycle derivatives according to Formula I, wherein $R_2$ is H or wherein $R_2$ is joined together with $R_7$ to form a 6-membered ring, optionally containing a heteroatom selected from O and S, and which atom is bonded to the 7-position of the indole ring.

Further preferred are the (indol-3-yl)-heterocycle derivatives of the invention wherein R, $R_5$, $R_5'$ and $R_6$ are H.

Also preferred are (indol-3-yl)-heterocycle derivatives according to formula I wherein $R_1$ is cyclohexyl or tetrahydropyranyl.

Especially preferred are the (indol-3-yl)-heterocycle derivatives according to Formula I where the heterocycle A is 1,2,4-oxadiazole ($X_1$ is N, $X_2$ is 0, $X_3$ is N), 1,2,4-thiadiazole ($X_1$ is N. $X_2$ is S, $X_3$ is N) or thiazole ($X_1$ is S, $X_2$ is CR, $X_3$ is N).

Specifically preferred (indol-3-yl)-heterocycle derivatives of the invention are:

7-Chloro-3-(5-{[N-ethyl-N-(2-methoxyethyl)amino]methyl}-[1,2,4]-thiadiazol-3-yl)-1-(tetrahydropyran-4-yl) methyl-1H-indole;

7-Chloro-3-{5-[(pyrrolidin-1-yl)methyl]-[1,2,4]-thiadiazol-3-yl}-1-(tetrahydropyran-4-yl)methyl-1H-indole;

7-Chloro-3-(5-{[N-ethyl-N-(2-hydroxyethyl)amino]methyl}-[1,2,4]-thiadiazol-3-yl)-1-(tetrahydropyran-4-yl) methyl-1H-indole;

7-Chloro-3-(4-{[N-(2-hydroxyethyl)-N-isopropylamino]methyl}-[1,3]-thiazol-2-yl)-1-(tetrahydropyran-4-yl)methyl-1H-indole;

7-Chloro-3-(4-{[N-ethyl-N-(2-hydroxyethyl)amino]methyl}[1,3]-thiazol-2-yl)-1-(tetrahydropyran-4-yl)methyl-1H-indole;

7-Chloro-3-(4-{[N-(2-methoxyethyl)-N-methylamino]methyl}-[1,3]-thiazol-2-yl)-1-(tetrahydropyran-4-yl)methyl-1H-indole;

7-Chloro-3-{5-[(2,2-dimethyl-pyrolidin-1-yl)methyl]-[1,2,4]oxadiazol-3-yl}-1-(tetrahydropyran-4-yl)methyl-1H-indole;

or a pharmaceutically acceptable salt thereof.

The (indol-3-yl)-heterocycle derivatives of the invention may be prepared by methods known in the art of organic chemistry in general.

(Indol-3-yl) heterocycle derivatives of Formula I can for instance be prepared from compounds of Formula II where Y is a leaving group, such as a halogen or alkylsulfonate group, by nucleophilic displacement of the leaving group with an amine of formula $NHR_3R_4$. Compounds of Formula II where Y is an alkylsulfonate group can be prepared from compounds of Formula II where Y is hydroxy, by reaction with an alkylsulfonyl halide in the presence of a base such as triethylamine.

(Indol-3-yl) heterocycles of Formula I where $R_5'$ is hydrogen can be prepared from compounds of Formula III by reductive amination, using an amine of formula $NHR_3R_4$ in the presence of a reducing agent such as sodium triacetoxyborohydride.

It is well known in the art that compounds of Formula II where Y is hydroxy and $R_5'$ is hydrogen can be inter-converted with compounds of Formula III, by oxidation and reduction using suitable oxidising and reducing agents, as described in Burke D. S., Danheiser, R. L. *Handbook of Reagents for Organic Synthesis: Oxidising and Reducing agents* (Wiley: N.Y. 1999). Likewise, compounds of Formula II where Y is hydroxy and $R_5$ and $R_5'$ are both hydrogen, and compounds of Formula III where $R_5$ is hydrogen, can be prepared from compounds of Formula IV where $R_8$ is hydrogen or $(C_{1-4})$alkyl, by reduction using suitable reducing agents. Compounds of Formula II where Y is hydroxy and $R_5'$ is $(C_{1-4})$alkyl can be prepared from compounds of Formula III by nucleophilic addition, using a $(C_{1-4})$alkyl metal reagent such as an alkyl Grignard reagent or alkyllithium.

Formula II

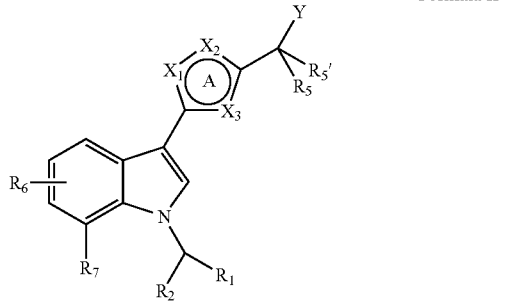

Formula III

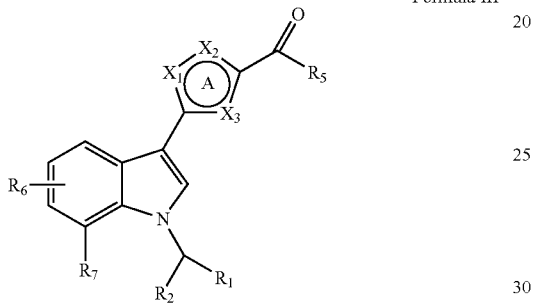

Formula IV

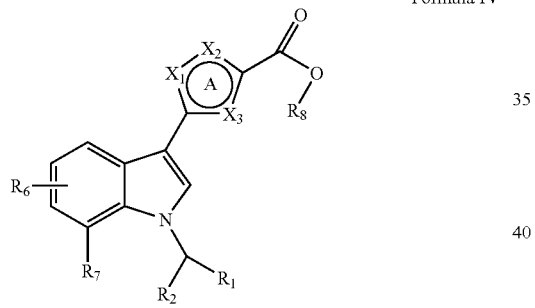

Compounds of Formula I, Formula II, Formula III or Formula IV can be prepared from compounds of Formula V to Formula XII inclusive, using methods well known in the art for constructing heterocyclic rings. Such methods are described in the general reference Katritzky, A. R.: *Comprehensive heterocyclic chemistry* (First Edition, Pergamon Press, 1984, see especially Volume 4, Part 3, Five-membered rings with one oxygen, sulfur or nitrogen atom and Volume 6, Part 4B, Five-membered rings with two or more oxygen, sulfur or nitrogen atoms).

Formula V

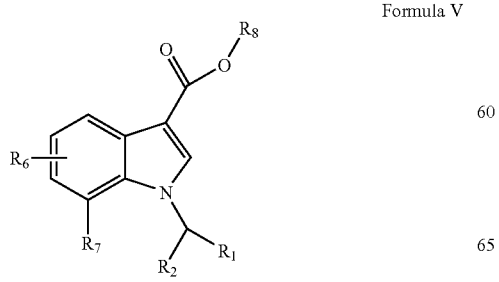

-continued

Formula VI

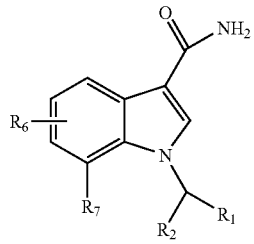

Formula VII

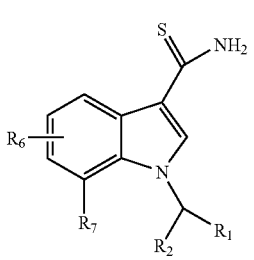

Formula VIII

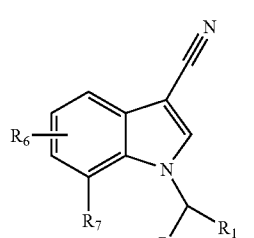

Formula IX

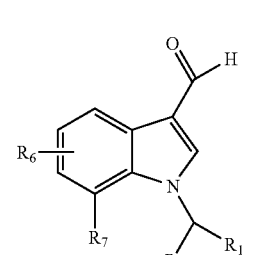

Formula X

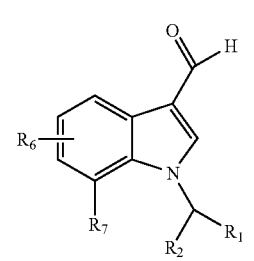

Formula XI

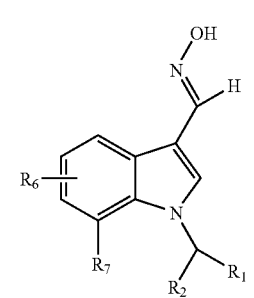

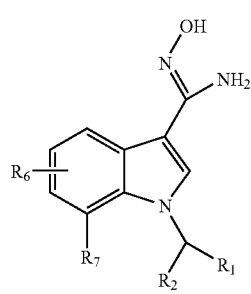

Formula XII

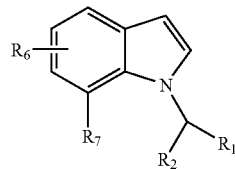

Formula XIII

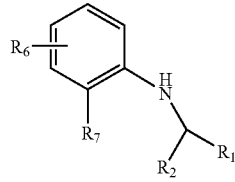

Formula XIV

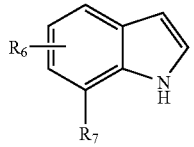

Formula XV

Compounds of Formula V to Formula XII inclusive, wherein $R_1$, $R_2$, $R_6$ and $R_7$ have the meanings as previously defined and $R_8$ is H or $(C_{1-4})$alkyl, can be prepared by literature procedures or modifications of literature procedures known to those persons skilled in the art.

For example, compounds of Formula VI can be prepared from compounds of Formula V, or activated derivatives thereof, by reaction with ammonia in a suitable solvent.

Compounds of Formula VII can be prepared from compounds of Formula VI using thionation reagents, such as phosphorus pentasulfide or Lawesson's reagent. Alternatively, compounds of Formula VII can be prepared from compounds of Formula VIII by reaction with thioacetamide in a solvent such as dimethylformamide. Compounds of Formula VIII can be prepared from compounds of Formula VI by dehydration, for example using trifluoroacetic anhydride in the presence of a base such as triethylamine.

Compounds of Formula X can be prepared from compounds of Formula IX by reaction with hydroxylamine in a suitable solvent.

Compounds of Formula XI where Y is $NH_2$ can be prepared from compounds of Formula V, or activated derivatives thereof, by reaction with cyanide anion to form an oxoacetonitrile, followed by reduction of the nitrile to a primary amine using a reducing agent, such as hydrogen gas in the presence of a catalyst such as palladium on charcoal.

Compounds of formula XII can be prepared from compounds of formula VIII by reaction with hydroxylamine in a suitable solvent.

Compounds of Formula V and compounds of Formula XI can be prepared by acylation of compounds of Formula XIII. For example, compounds of Formula V where $R_8$ is hydrogen can be prepared by acylation of compounds of Formula XIII using trifluoroacetic anyhydride in a solvent such as dimethylformamide, followed by hydrolysis using aqueous sodium hydroxide at an elevated temperature. Compounds of Formula XI where Y is chlorine can be prepared by acylation of compounds of Formula XII using chloroacetyl chloride, in the presence of a base such as pyridine. Compounds of formula IX can be prepared from compounds of Formula XIII by formylation, for example using the Vilsmeier reaction (for a review see Jutz, *Adv. Org. Chem.* 9, pt. 1, 225-342, 1976).

Alternatively, compounds of Formula V can be prepared from compounds of Formula XIV using procedures described by Wijngaarden et al. (*J. Med. Chem.* 36, 3693-3699, 1993) or Hwu et al. (*J. Org. Chem.* 59, 1577-1582, 1994) or modifications of these procedures.

Compounds of Formula XII can be prepared by literature procedures or modifications of literature procedures known to those persons skilled in the art. For example, compounds of Formula XIII can be prepared by alkylation of compounds of formula XV, by treatment with a base such as sodium hydride, followed by reaction with an alkylating agent $R_1R_2CHY$, where Y is a leaving group, such as a halogen or alkylsulfonate group. Compounds of Formula XV can be obtained from commercial sources, prepared by literature procedures or modifications of literature procedures known to those persons skilled in the art.

Alternatively, compounds of Formula XIII can be prepared from compounds of Formula XIV using the Fischer indole synthesis or modifications thereof (*Chem. Rev.* 69, 227-250, 1969).

Compounds of Formula XIV can be prepared by literature procedures or modifications of literature procedures known to those persons skilled in the art. For example compounds of Formula XIV where $R_2$ is joined together with $R_7$ to form a 6-membered carbocyclic ring can be prepared from compounds of Formula XVI by reduction, using a reducing agent such as sodium borohydride in the presence of a catalyst such as nickel (II) chloride. Compounds of Formula XVI can for example be prepared by a coupling reaction, such as reaction of a 2-chloroquinoline with a Grignard reagent, in the presence of a nickel (II) catalyst.

Compounds of Formula XIV where $R_2$ is joined together with $R_7$ to form a 6-membered ring containing oxygen or sulfur can be prepared by reaction of a compound of Formula XVII where Z is OH or SH, with a compound of Formula XVIII, where Y is a leaving group, to form an ether or thioether, followed by reduction of the nitro group to an amine and reductive cyclisation. The reduction and cyclisation can for example be carried out using hydrogen gas in the presence of a catalyst such as palladium on charcoal.

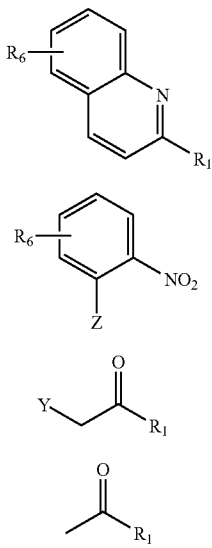

Formula XVI

Formula XVII

Formula XVIII

Formula XIX

Compounds of Formula XVII and compounds of Formula XVIII can be obtained from commercial sources, prepared by literature procedures or modifications of literature procedures known to those persons skilled in the art. For example, compounds of Formula XVIII where Y is bromine can be prepared from compounds of Formula XIX using a brominating agent such as bromine in a solvent such as methanol.

Compounds of Formula I, Formula II, Formula III or Formula IV may alternatively be prepared from compounds of Formula XX using transition metal catalysed coupling reactions, as described in the general reference Hegedus, L. S. *Transition Metals in the Synthesis of Complex Organic Molecules* (Second Edition, University Science: Sausalito 1999).

For example, compounds of Formula III may be prepared by the reaction of compounds of Formula XX, where $Y_1$ is halogen, with compounds of Formula XXI, where $Y_2$ is a boronic acid or a boronic acid ester, using a Suzuki reaction (*Chem. Rev.* 95, 2457-2483, 1995) or a modification thereof.

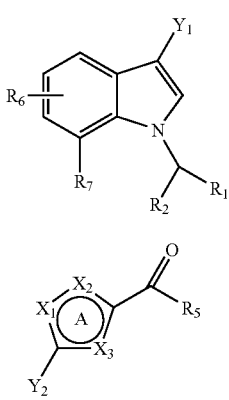

Formula XX

Formula XXI

Compounds of Formula XX and compounds of Formula XXI can be obtained from commercial sources, prepared by literature procedures or modifications of literature procedures known to those persons skilled in the art. For example, compounds of Formula XX where $Y_1$ is bromine may be prepared by bromination of a compound of Formula XIII using bromine in a solvent such as dimethylformamide.

It will be appreciated by those persons skilled in the art that the indole nitrogen may be temporarily protected during the transformations described above using a protecting group, such as an arylsulfonyl group, to be deprotected and alkylated at a later stage in the synthesis. It will further be appreciated that such protecting groups may be used to modify the stability of intermediates and the reactivity of the indole ring towards electrophiles. Suitable protecting groups are described in Kocienski, P. J.: *Protecting Groups*, Thieme, Stuttgart; New York, 1994.

The skilled person will likewise appreciate that various (indol-3-yl) heterocycle derivatives of Formula I can be obtained by appropriate conversion reactions of functional groups corresponding to certain of the substituents $R_3$-$R_7$. For example, compounds of Formula I wherein $R_3$ or $R_4$ is a C1 to C6 linear, branched or cyclic alkyl group optionally substituted with hydroxyl, $(C_{1-4})$alkyloxy, $(C_{1-4})$alkylthio, $(C_{1-4})$-alkylsulfonyl or cyano, can be prepared by the reaction of a compound of Formula I wherein $R_3$ or $R_4$ is hydrogen with a C1 to C6 alkyl halide or a functionalised C1 to C6 alkyl halide, in the presence of a base such as potassium carbonate.

The (indol-3-yl)-heterocycle derivatives of Formula I and their salts may contain at least one centre of chirality, and exist therefore as stereoisomers, including enantiomers and diastereomers. The present invention includes the aforementioned stereoisomers within its scope and each of the individual R and S enantiomers of the compounds of Formula I and their salts, substantially free, i.e. associated with less than 5%, preferably less than 2%, in particular less than 1% of the other enantiomer, and mixtures of such enantiomers in any proportions including the racemic mixtures containing substantially equal amounts of the two enantiomers.

Methods for asymmetric synthesis or chiral separation whereby the pure stereoisomers are obtained are well known in the art, e.g. synthesis with chiral induction or starting from commercially available chiral substrates, or separation of stereoisomers, for example using chromatography on chiral media or by crystallisation with a chiral counter-ion.

Pharmaceutically acceptable salts may be obtained by treating a free base of a compound of Formula I with a mineral acid such as hydrochloric acid, hydrobromic acid, phosphoric acid and sulfuric acid, or an organic acid such as for example ascorbic acid, citric acid, tartaric acid, lactic acid, maleic acid, malonic acid, fumaric acid, glycolic acid, succinic acid, propionic acid, acetic acid and methane sulfonic acid.

The compounds of the invention may exist in unsolvated as well as in solvated forms with pharmaceutically acceptable solvents such as water, ethanol and the like. In general, the solvated forms are considered equivalent to the unsolvated forms for the purpose of the invention.

The present invention further provides pharmaceutical compositions comprising a (indol-3-yl)-heterocycle derivative according to general Formula I, or a pharmaceutically acceptable salt thereof, in admixture with pharmaceutically acceptable auxiliaries, and optionally other therapeutic agents. The term "acceptable" means being compatible with the other ingredients of the composition and not deleterious to the recipients thereof. Compositions include e.g. those suitable for oral, sublingual, subcutaneous, intravenous, epidural, intrathecal, intramuscular, transdermal, pulmonary, local, or rectal administration, and the like, all in unit dosage forms for administration. A preferred route of administration is the intravenous route.

For oral administration, the active ingredient may be presented as discrete units, such as tablets, capsules, powders, granulates, solutions, suspensions, and the like. For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al., Remington: *The Science and Practice of Pharmacy* (20th Edition, Lippincott Williams & Wilkins, 2000, see especially Part 5: Pharmaceutical Manufacturing), the active agent may be compressed into solid dosage units, such as pills, tablets, or be processed into capsules, suppositories or patches. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The invention further includes a pharmaceutical composition, as hereinbefore described, in combination with packaging material suitable for said composition, said packaging material including instructions for the use of the composition for the use as hereinbefore described.

The (indol-3-yl)-heterocycle derivatives of the invention were found to be agonists of the CB1 receptor, as determined in a human CB1 reporter assay using CHO cells. Methods to determine receptor binding as well as in vitro biological activity of cannabinoid receptor modulators are well known in the art. In general, expressed receptor is contacted with the compound to be tested and binding or stimulation or inhibition of a functional response is measured.

To measure a functional response isolated DNA encoding the CB1 receptor gene, preferably the human receptor, is expressed in suitable host cells. Such a cell might be the Chinese Hamster Ovary cell, but other cells are also suitable. Preferably the cells are of mammalian origin.

Methods to construct recombinant CB1 expressing cell lines are well known in the art (Sambrook et al., Molecular Cloning: a Laboratory Manual, Cold Spring Harbor Laboratory Press, Cold Spring Harbor, latest edition). Expression of the receptor is attained by expression of the DNA encoding the desired protein. Techniques for ligation of additional sequences and construction of suitable expression systems are all, by now, well known in the art. Portions or all of the DNA encoding the desired protein can be constructed synthetically using standard solid phase techniques, preferably to include restriction sites for ease of ligation. Suitable control elements for transcription and translation of the included coding sequence can be provided to the DNA coding sequences. As is well known, expression systems are now available which are compatible with a wide variety of hosts, including prokaryotic hosts such as bacteria and eukaryotic hosts such as yeast, plant cells, insect cells, mammalian cells, avian cells and the like.

Cells expressing the receptor are then contacted with the test compound to observe binding, or stimulation or inhibition of a functional response.

Alternatively isolated cell membranes containing the expressed CB1 (or CB2) receptor may be used to measure binding of compound.

For measurement of binding radioactively or fluorescently labelled compounds may be used. The most widely used radiolabelled cannabinoid probe is [$^3$H]CP55940, which has approximately equal affinity for CB1 and CB2 binding sites.

Another assay involves screening for cannabinoid CB1 agonist compounds by determining the second messenger response, such as for example measurement of receptor mediated changes in cAMP or MAPkinase pathways. Thus, such a method involves expression of the CB1 receptor on the cell surface of a host cell and exposing the cell to the test compound. The second messenger response is then measured. The level of second messenger will be reduced or increased, depending on the effect of the test compound upon binding to the receptor.

In addition to direct measurement of e.g. cAMP levels in the exposed cell, cells can be used which in addition to transfection with receptor encoding DNA are also transfected with a second DNA encoding a reporter gene, the expression of which correlates with receptor activation. In general, reporter gene expression might be controlled by any response element reacting to changing levels of second messenger. Suitable reporter genes are e.g. LacZ, alkaline phosphatase, firefly luciferase and green fluorescence protein. The principles of such transactivation assays are well known in the art and are described e.g. in Stratowa, Ch, Himmler, A. and Czernilofsky, A. P., *Curr. Opin. Biotechnol.* 6, 574 (1995). For selecting active agonist compounds on the CB1 receptor the $EC_{50}$ value must be $<10^{-5}$ M, preferably $<10^{-7}$ M.

The compounds may be used as analgesic agents in the treatment of pain such as for example peri-operative pain, chronic pain, neuropathic pain, cancer pain and pain and spasticity associated with multiple sclerosis.

Cannabinoid agonists of the invention would also potentially be useful in the treatment of other disorders including multiple sclerosis, spasticity, inflammation, glaucoma, nausea and emesis, loss of appetite, sleep disturbances, respiratory disorders, allergies, epilepsy, migraine, cardiovascular disorders, neurodegenerative disorders, anxiety, traumatic brain injury and stroke.

The compounds could also be used in conjunction with other drugs, for example analgesic drugs such as opioids and non-steroidal anti-inflammatory drugs (NSAIDs), including COX-2 selective inhibitors.

The compounds of the invention may be administered to humans in a sufficient amount and for a sufficient amount of time to alleviate the symptoms. Illustratively, dosage levels for humans can be in the range of 0.001-50 mg per kg body weight, preferably in a dosage of 0.01-20 mg per kg body weight.

The invention is illustrated by the following Examples.

General Methods

Microwave reactions were performed using an Emrys Optimizer™ (Personal Chemistry) unless otherwise stated. Flash column chromatography was performed on silica gel. Semi-preparative high pressure liquid chromatography (semi-prep. HPLC) was performed using the methods outlined below:

Method (i): Agilent CombiHT (SB-C18, 5 μm) 12 mm ID×100 mm; 5-95% acetonitrile-water over a 9 minute gradient; 25 ml/min; 0.1% trifluoroacetic acid buffer; detection by UV at 254 nm.

Method (ii): Waters Xterra (RP18, 5 μm) 30 mm×100 mm; 10-100% acetonitrile-water over a 25 minute gradient; 30 ml/min; 0.1% trifluoroacetic acid buffer; detection by UV at 254 nm.

$^1$H NMR coupling constants are given in Hz.

EXAMPLE 1

1-(Cyclohexyl)methyl-3-{5-[(dimethylamino)methyl]-[1,2,4]oxadiazol-3-yl}-7-methoxy-1H-indole, hydrochloride salt A solution of 7-methoxyindole (45.0 g, 306 mmol) in dimethylformamide (360 ml) was cooled to 5° C. under nitrogen and trifluoroacetic anhydride (60.5 ml, 433 mmol) was added over 20 minutes, maintaining the temperature below 10° C. The mixture was stirred at 5-10° C. for 2 h, then poured into water (1600 ml). The resulting suspension was stirred for 15 minutes and the 7-methoxy-3-[(trifluoromethyl)carbonyl]-1H-indole precipitate was filtered off, washing with water to neutrality.

The damp solid was suspended in 4 M aqueous sodium hydroxide (1700 ml) and heated to reflux with stirring for 2 h. The mixture was cooled and washed with diethyl ether (2×400 ml). The aqueous phase was then acidified to pH 1 using 5 M hydrochloric acid and the resulting fine precipitate filtered off, washed with water to neutrality and dried to afford 7-methoxy-1H-indole-3-carboxylic acid as a pink solid (42.7 g). To a solution of 7-methoxy-1H-indole-3-carboxylic acid (42.7 g, 224 mmol) in di-methylformamide (1250 ml) at 10° C. under nitrogen was added sodium hydride (60% dispersion in mineral oil, 23.0 g, 575 mmol) portionwise over 20 minutes, maintaining the temperature below 15° C. The cooling bath was removed and the suspension stirred for 90 minutes. Cyclohexylmethyl bromide (64.7 ml, 464 mmol) was added. The mixture was heated at 60° C. with stirring for 3 h. The mixture was cooled to 10° C. and poured into water (3600 ml). The emulsion was washed with diethyl ether (3×500 ml). The aqueous phase was acidified to pH 1 using 5 M hydrochloric acid and the precipitate filtered off, washed with water to neutrality and dried to afford 1-(cyclohexyl)methyl-7-methoxy-1H-indole-3-carboxylic acid (55 g) as a white solid. Oxalyl chloride (12.4 g, 97.4 mmol) was added dropwise to a mixture of 1-(cyclohexyl)methyl-7-methoxy-1H-indole-3-carboxylic acid (7.0 g, 24.4 mmol) and dichloromethane (150 ml) under ice-water cooling and the resulting mixture was stirred at room temperate for 18 h. Dichloromethane and excess oxalyl chloride were removed by evaporation and the obtained residue was mixed with dichloromethane (150 ml). Ammonia gas was bubbled into the resulting mixture for 30 min under ice-water bath cooling. The reaction mixture was concentrated in vacuo, then the obtained solid was triturated sequentially with 0.5 M hydrochloric acid, 5% aqueous sodium carbonate, and water, and dried under reduced pressure to afford 1-(cyclohexyl)methyl-7-methoxy-1H-indole-3-carboxylic acid amide (5.1 g) as a brown solid.

Trifluoroacetic anhydride (12.0 g, 57.1 mmol) was added dropwise to a mixture of 1-(cyclohexyl)methyl-7-methoxy-1H-indole-3-carboxylic acid amide (4.1 g, 14.3 mmol), triethylamine (11.6 g, 115 mmol), and 1,4-dioxane (250 ml) under ice-water cooling. The resulting mixture was stirred at room temperature for 12 h. Water (30 ml) was added and the resulting mixture was concentrated in vacuo. Water (300 ml) was added to the obtained residue, and the mixture was extracted with dichloromethane (4×300 ml). The organic layers were combined, washed with 5% aqueous sodium hydrogen carbonate and brine, dried over magnesium sulfate, and concentrated in vacuo. The obtained residue was purified by column chromatography eluting with 10% (v/v) ethyl acetate in n-heptane to afford 1-(cyclohexyl)methyl-7-methoxy-1H-indole-3-carbonitrile as a crystalline solid (2.48 g).

Hydroxylamine hydrochloride (966 mg, 13.9 mmol) was added to a mixture of 1-(cyclohexyl)methyl-7-methoxy-1H-indole-3-carbonitrile (2.48 g, 9.24 mmol), triethylamine (1.41 g, 13.9 mmol), and ethanol (50 ml), then the resulting mixture was stirred at reflux for 20 h. After being cooled to room temperature, the reaction mixture was concentrated in vacuo. The obtained residue was mixed with water (150 ml), adjusted to pH 10 by the addition of aqueous sodium hydroxide and extracted with dichloromethane (4×100 ml). The organic layers were combined, washed with brine, dried over magnesium sulfate, and concentrated in vacuo. The obtained residue was purified by column chromatography eluting with 10% (v/v) acetone in dichloromethane to give 1-(cyclohexyl)methyl-N-hydroxy-7-methoxy-1H-indole-3-carboxamidine (940 mg).

Molecular sieves (4 Å, powdered, 200 mg) were added to a suspension of 1-(cyclohexyl)methyl-N-hydroxy-7-methoxy-1H-indole-3-carboxamidine (250 mg, 0.829 mmol) in tetrahydrofuran (6 ml) under nitrogen, and the mixture was stirred at room temperature for 30 min. Sodium hydride (60% suspension in oil, 36 mg, 0.900 mmol) was added, then the resulting mixture was stirred at 60° C. for 20 min. The reaction mixture was cooled to room temperature and N,N-dimethylglycine methyl ester (194 mg, 1.66 mmol) was added to the mixture. The resulting mixture was stirred at reflux temperature for 2 h and then concentrated in vacuo. The obtained residue was mixed with dichloromethane (200 ml), washed with 5% aqueous sodium carbonate, dried over magnesium sulfate and concentrated in vacuo. The obtained oil was purified by flash column chromatography eluting with 0.6% (v/v) methanol in dichloromethane to afford an oil. This oil was dissolved in isopropanol (3 ml), then hydrogen chloride (1M solution in diethyl ether; 3 ml) was added to the solution. The resulting mixture was concentrated in vacuo to afford the title compound (1:1 hydrochloride salt) (66 mg).

$^1$H NMR (400 MHz, CD$_3$OD) δ 0.96-1.30 (5H, m), 1.52-1.94 (6H, m), 3.13 (6H, s), 3.97 (3H, s), 4.30 (2H, d, J 6.8), 4.83 (2H, s), 6.81 (1H, d, J 8.0), 7.13 (1H, dd, J 8.0, 8.0) 7.71 (1H, d, J 8.0), 7.85 (1H, s). EsIMS: m/z 369.2 [M+H]$^+$.

EXAMPLE 2

The method of Example 1 was further used to prepare the following compounds, using alternative synthetic or commercially available amino acid esters instead of N,N-dimethylglycine methyl ester.

Methods for the Synthesis of Amino Acid Ester Intermediates

Method A

Benzyl bromoacetate (500 mg, 2.18 mmol) was added to a mixture of pyrrolidine (171 mg, 2.40 mmol) and sodium carbonate (254 mg, 2.40 mmol) in tetrahydrofuran (7 ml). The mixture was stirred at room temperature for 18 h, then concentrated in vacuo. The residue was mixed with water (200 ml) and extracted with dichloromethane (3×100 ml). The organic layers were combined, dried over sodium sulfate and concentrated in vacuo. Purification by flash column chromatography eluting with 0-10% (v/v) methanol in dichloromethane afforded pyrrolidin-1-yl acetic acid benzyl ester (230 mg, 1.05 mmol).

Method B

Methyl bromoacetate (199 µl, 2.10 mmol) was added to a mixture of (S)-2-methoxymethyl pyrrolidine (268 µl, 2.17 mmol), potassium carbonate (319 mg, 2.31 mmol) and sodium iodide (315 mg, 2.10 mmol) in acetonitrile (3 ml). The mixture was subjected to microwave irradiation for 5 min at 160° C., then partitioned between dichloromethane and water. The aqueous layer was extracted with dichloromethane and the combined organic layers were washed with brine, dried over sodium sulfate and concentrated in vacuo. Purification by flash column chromatography eluting with 0-10% (v/v) methanol in dichloromethane afforded (S)-(2-methoxymethyl-pyrrolidin-1-yl) acetic acid methyl ester (133 mg, 0.71 mmol).

Method C

To a solution of sulfuric acid (3.5 ml, 65.3 mmol) in methanol (45 ml) was added D-proline (10.0 g, 86.9 mmol). The mixture was refluxed with stirring for 18 h. The solution was then cooled to 0° C. and neutralised by addition of aqueous potassium carbonate (2.5 M; 10 ml). Formaldehyde (37% solution in water; 11 ml, 136 mmol) was added and the mixture stirred at 0° C. for 15 minutes. Sodium borohydride (1.6 g, 42.3 mmol) was added at 0° C. and the mixture was stirred at room temperature for 3 h. The precipitate was filtered off and the filtrate was partitioned between dichloromethane and water. The isolated aqueous layer was adjusted to pH 10 using solid sodium carbonate and extracted with dichloromethane. The combined organic layers were dried over sodium sulfate and concentrated in vacuo to afford crude (R)-1-methylpyrrolidine-2-carboxylic acid methyl ester (13.13 g).

A portion of this crude product (5.0 g) was purified by flash column chromatography eluting with 0-2% (v/v) methanol in dichloromethane to afford (R)-1-methylpyrrolidine-2-carboxylic acid methyl ester (1.30 g).

2A: 1-(Cyclohexyl)methyl-7-methoxy-3-{5-[(pyrrolidin-1-yl)methyl]-[1,2,4]oxadiazol-3-y}-1H-indole, hydrochloride salt The title compound was prepared following the method of Example 1, using pyrrolidin-1-yl acetic acid benzyl ester, prepared according to Method A. $^1$H NMR (400 MHz, CD$_3$OD) δ 0.98-1.31 (5H, m), 1.54-1.94 (6H, m), 2.10-2.24 (4H, m), 3.46-3.74 (4H, m), 3.97 (3H, s), 4.30 (2H, d, J 7.2), 4.86 (2H, s), 6.81 (1H, d, J 8.0), 7.14 (1H, dd, J 8.0, 8.0), 7.70 (1H, s). EsIMS: m/z 395.2 [M+H]$^+$.

2B: 1-(Cyclohexyl)methyl-3-{5-[(N-ethyl-N-isopropylamino)methyl]-[1,2,4]oxadiazol-3-yl}-7-methoxy-1H-indole, hydrochloride salt The title compound was prepared using (N-ethyl-N-isopropylamino)acetic acid methyl ester, which was prepared according to Method A, using methyl bromoacetate and N-ethyl isopropylamine. EsIMS: m/z 411.1 [M+H]$^+$.

2C: 1-(Cyclohexyl)methyl-7-methoxy-3-(5-{[bis-(2-methoxyethyl)amino]methyl}-[1,2,4]oxadiazol-3-yl)-1H-indole, hydrochloride salt The title compound was prepared using [bis-(2-methoxyethyl)amino]acetic acid methyl ester, which was prepared according to Method A, using methyl bromoacetate and bis-(2-methoxyethyl)amine. EsIMS: m/z 457.5 [M+H]$^+$.

2D: 1-(Cyclohexyl)methyl-3-{5-[1-(dimethylamino) ethyl]-[1,2,4]oxadiazol-3-yl-}-7-methoxy-1H-indole, hydrochloride salt The title compound was prepared using 2-dimethylamino propionic acid methyl ester, which was prepared according to Method A, using methyl-2-bromopropionate and dimethylamine. EsIMS: m/z 383.0 [M+H]$^+$.

2E: (S)-1-(Cyclohexyl)methyl-7-methoxy-3-{5-[(2-methoxymethylpyrrolidin-1-yl)methyl]-[1,2,4]oxadiazol-3-yl}-1H-indole, hydrochloride salt The title compound was prepared using (S)-(2-methoxymethyl-pyrrolidin-1-yl) acetic acid methyl ester, which was prepared according to Method B. EsIMS: m/z 439.3 [M+H]$^+$.

2F: (R)-1-(Cyclohexyl)methyl-7-methoxy-3-{5-[(2-methoxymethylpyrrolidin-1-yl) methyl]-[1,2,4]oxadiazol-3-yl}-1H-indole hydrochloride salt The title compound was prepared using (R)-(2-methoxymethyl-pyrrolidin-1-yl) acetic acid methyl ester, which was prepared according to Method B, using (R)-2-methoxy-methyl pyrrolidine.
EsIMS: m/z 439.1 [M+H]$^+$; $[\alpha]_D^{22}$+21.6° (c=0.8 mg/ml in chloroform).

2G: (R)-1-(Cyclohexyl)methyl-7-methoxy-3-[5-(1-methylpyrrolidin-2-yl)-[1,2,4]oxadiazol-3-yl]-1H-indole, hydrochloride salt The title compound was prepared using (R)-1-methylpyrrolidine-2-carboxylic acid methyl ester, which was prepared according to Method C. EsIMS: m/z 395.0 [M+H]$^+$; $[\alpha]_D^{22}$+50.1°(c=1.70 mg/ml in chloroform).

2H: (S)-1-(Cyclohexyl)methyl-7-methoxy-3-[5-(1-methylpyrrolidin-2-yl)-[1,2,4]oxadiazol-3-yl]-1H-indole, hydrochloride salt The title compound was prepared using (S)-1-methylpyrrolidine-2-carboxylic acid methyl ester, which was prepared according to Method C, using L-proline instead of D-proline. EsIMS: m/z 395.0 [M+H]$^+$. $[\alpha]_D^{22}$-51.7°(c=1.35 mg/ml in chloroform).

2I: 1-(Cyclohexyl)methyl-7-methoxy-3-[5-(1-methylpiperidin-2-yl)-[1,2,4]oxadiazol-3-yl]-1H-indole, hydrochloride salt The title compound was prepared following the method of Example 1, using ethyl 1-methyl pipecolinate instead of N,N-dimethylglycine methyl ester. EsIMS: m/z 409.3 [M+H]$^+$.

EXAMPLE 3

1-(Cyclohexyl)methyl-3-[(5-aminomethyl)-[1,2,4] oxadiazol-3-yl]-7-methoxy-1H-indole, hydrochloride salt Molecular sieves (4 Å, powdered, 300 mg) were added to a suspension of 1-(cyclohexyl)methyl-N-hydroxy-7-methoxy-1H-indole-3-carboxamidine (500 mg, 1.66 mmol) in tetrahydrofuran (10 ml), and the resulting mixture was stirred at room temperature for 30 min. Sodium hydride (60% suspension in oil, 100 mg, 2.55 mmol) was added and the resulting mixture was stirred at 65° C. for 20 min. The reaction mixture was cooled to room temperature and N-Boc-glycine N-hydroxysuccinimide ester (871 mg, 3.32 mmol) was added to the mixture. The resulting mixture was heated to reflux with stirring for 2 h, then cooled to room temperature. Aqueous sodium hydroxide (4M; 5 ml) was added and the resulting mixture was stirred for 14 h. The reaction mixture was concentrated in vacuo, then the obtained residue was mixed with water (200 ml). The resulting mixture was extracted with dichloromethane (4×200 ml). The organic layers were combined, washed with brine, dried over magnesium sulfate and concentrated in vacuo. The obtained oil was purified by column chromatography eluting with 0.4% (v/v) methanol in dichloromethane to afford ({3-[1-(cyclohexyl)-methyl-7-methoxy-1H-indol-3-yl][1,2,4]oxadiazol-5-yl}methyl)carbamic acid tert-buty ester (125 mg).

A mixture of ({3-[1-(cyclohexyl)methyl-7-methoxy-1H-indol-3-yl][1,2,4]oxadiazol-5-yl}methyl)carbamic acid tert-buty ester (110 mg, 0.25 mmol) and trifluoroacetic acid (4 ml) was stirred at room temperature for 1.5 h. The reaction mixture was carefully poured into 5% aqueous sodium carbonate (200 ml) and the resulting mixture was extracted with dichloromethane (4×200 ml). The organic layers were combined, then washed with brine, dried over magnesium sulfate, and concentrated in vacuo. The obtained oil was purified by column chromatography eluting with 1.5% (v/v) methanol in dichloromethane to afford the free base of the title compound as a yellow oil. This oil was dissolved in diethyl ether, and then hydrogen chloride (1M solution in diethyl ether; 3 ml) was added to the solution. The resulting mixture was concentrated in vacuo to afford the title compound as a 1:1 hydrochloride salt (71 mg). $^1$H NMR (400 MHz, CD$_3$OD) δ 0.98-1.29 (5H, m), 1.52-1.78 (5H, m), 1.79-1.94 (1H, m), 3.98 (3H, s), 4.31 (2H, d, J 7.2), 4.55 (2H, s), 6.81 (1H, d, J 7.6), 7.14 (1H, dd, J 7.6, 8.0) 7.72 (1H, d, J 8.0), 7.83 (1H, s). EsIMS: m/z 341.1 [M+H]$^+$.

EXAMPLE 4

1-(Cyclohexyl)methyl-3-{5-[(dimethylamino)methyl]-[1,2,4]oxadiazol-3-yl}-7-fluoro-1H-indole, hydrochloride salt The title compound was prepared following the method of Example 1, using 7-fluoroindole instead of 7-methoxyindole. EsIMS: m/z 357.3 [M+H]$^+$, 247.4.

EXAMPLE 5

7-Chloro-1-(cyclohexyl)methyl-3-{5-[(dimethylamino)methyl]-[1,2,4]oxadiazol-3-yl}-1H-indole, hydrochloride salt The title compound was prepared following the method of Example 1, using 7-chloroindole instead of 7-methoxyindole. EsIMS: m/z 375.1, 373.1 [M+H]$^+$.

EXAMPLE 6

1-(Cyclohexyl)methyl-3-(5-{[N-isopropyl-N-(2-methoxyethyl)amino]methyl}-[1,2,4]-triazol-3-yl)-7-methoxy-1H-indole, hydrochloride salt Hydrochloride gas was bubbled, for 30 mins, through a cooled (0° C.) solution of 1-(cyclohexyl)methyl-7-methoxy-1H-indole-3-carbonitrile (prepared as described in Example 1; 3.15 g, 11.0 mmol) in methanol (200 ml). The resulting mixture was left to stand for 72 h before being concentrated, by two thirds, in vacuo. Crystallisation of the product was achieved on addition of diethyl ether, and the resultant solid was collected via filtration to give 1-(cyclohexyl)methyl-7-methoxy-1H-indole-3-carboximidic acid methyl ester as the hydrochloride salt (3.82 g). 1-(Cyclohexyl)methyl-7-methoxy-1H-indole-3-carboximidic acid methyl ester hydrochloride salt (0.10 g, 0.297 mmol), hydrazine hydrate (0.289 ml, 5.94 mmol), aluminium chloride (39.6 mg, 0.297 mmol) and toluene (18 ml) were combined and the mixture was subjected to microwave irradiation for 60 min at 120° C. The resultant mixture was concentrated in vacuo, re-dissolved in toluene and concentrated in vacuo twice more. The obtained residue was suspended in a toluene/acetonitrile mixture (12/1) (19.5 ml) and chloroacetylchloride (0.118 ml, 1.49 mmol) added, before the mixture was subjected to microwave irradiation for 12 min at 120° C. The resultant mixture was concentrated in vacuo and re-dissolved in acetonitrile (3 ml). N-(2-methoxyethyl)isopropylamine (0.068 ml, 0.446 mmol), potassium carbonate (45.2 mg, 0.327 mmol) and sodium iodide (44 mg, 0.297 mmol) was added and the mixture was subjected to microwave irradiation for 5 min at 160° C. before being left to stand for 72 hours and then concentrated in vacuo. The obtained residue was purified by column chromatography eluting with 2.5%-5% (v/v) methanol in dichloromethane to afford the title compound as a 1:1 hydrochloride salt (46 mg). $^1$H NMR (400 MHz, CD$_3$OD): 0.95-1.12 (2H, m), 1.13-1.24 (3H, m), 1.50 (6H, s (br)), 1.55-1.73 (5H, m), 1.79-1.93 (1H, m), 3.34-3.50 (5H, m), 3.70-3.99 (6H, m), 4.24 (2H, d, J 6.4), 4.67 (2H, s (br)), 6.70 (1H, d, J 7.7), 7.16 (1H, t, J 7.7), 7.95 (1H, d, J 7.7), 8.02 (1H, s (br)); EsIMS: m/z 440.3 [M+H]$^+$.

EXAMPLE 7

1-(Cyclohexyl)methyl-3-{5-[(diethylamino)methyl]-[1,2,4]-thiadiazol-3-yl}-7-methoxy-1H-indole, hydrochloride salt To a suspension of 1-(cyclohexyl)methyl-7-methoxy-1H-indole-3-carboxylic acid amide (prepared from 7-methoxyindole as described in Example 1; 4.0 g, 14 mmol) in tetrahydrofuran (120 ml) was added chlorocarbonylsulfenyl chloride (2.4 ml, 28.4 mmol) and the reaction mixture was heated at reflux for 15 minutes and allowed to cool. The solvent and excess reagent were then removed in vacuo to leave 5-(1-cyclohexylmethyl-7-methoxy-1H-indole)-[1,3,4]-oxathiazol-2-one (5.2 g, 14.4 mmol) as a pink solid.

To a suspension of 5-(1-cyclohexylmethyl-7-methoxy-1H-indole)-[1,3,4]-oxathiazol-2-one (1.0 g, 2.77 mmol) in m-xylene (15 ml) was added ethylcyanoformate (2.74 ml, 27.7 mmol) and the reaction subjected to microwave irradiation at 160° C. for 10 min using an Emrys™ Optimizer EXP. The reaction was repeated three times on the same scale, combined and purified by flash column chromatography eluting with 0-50% (v/v) dichloromethane in heptane to give 3-(1-cyclohexylmethyl-7-methoxy-1H-indol-3-yl)-[1,2,4]thiadiazole-5-carboxylic acid ethyl ester (4.38 g, 11 mmol) as a white solid.

To a cooled solution (ice/methanol bath) of 3-(1-cyclohexylmethyl-7-methoxy-1H-indol-3-yl)-[1,2,4]thiadiazole-5-carboxylic acid ethyl ester (4.0 g, 10 mmol) in tetrahydrofuran (80 ml) and methanol (80 ml) was added sodium borohydride portion-wise. The reaction was stirred for a further 20 minutes and then quenched with 1M hydrochloric acid (20 ml). The methanol and tetrahydrofuran were removed in vacuo and dichloromethane (200 ml) and 2M hydrochloric acid (50 ml) were added. The organics were separated and washed with brine (50 ml), dried over magnesium sulfate and the solvent removed in vacuo. The resulting residue was purified by flash column chromatography eluting with 50% (v/v) diethyl ether in heptane to give [3-(1-cyclohexylmethyl-7-methoxy-1H-indol-3-yl)-[1,2,4]thiadiazol-5-yl]-methanol (3.15 g, 8.8 mmol) as a light pink solid.

To a cooled solution (ice/methanol bath) of [3-(1-cyclohexylmethyl-7-methoxy-1H-indol-3-yl)-[1,2,4]thiadiazol-5-yl]-methanol (2.3 g, 6.4 mmol) in dichloromethane (150 ml) was added methanesulfonyl chloride (0.595 ml, 7.68 mmol) and triethylamine (1.16 ml, 8.32 mmol) sequentially. The reaction was allowed to stir for 10 min and then poured into a separating funnel. The organics were washed with 5% aqueous sodium carbonate solution (2×100 ml), brine (100 ml), dried over magnesium sulfate and the solvent removed in vacuo to afford methanesulfonic acid 3-(1-cyclohexylmethyl-7-methoxy-1H-indol-3-yl)-[1,2,4]thiadiazol-5-ylmethyl ester (2.9 g, 6.7 mmol) which was used without further purification.

To a solution of methanesulfonic acid 3-(1-cyclohexylmethyl-7-methoxy-1H-indol-3-yl)-[1,2,4]thiadiazol-5-ylmethyl ester (93 mg, 0.2 mmol) in tetrahydrofuran (1 ml) was added diethylamine (0.22 ml, 2.13 mmol) and the reaction subjected to microwave irradiation at 150° C. for 15 minutes. The reaction was poured into a separating funnel and diluted with dichloromethane (40 ml). The combined organics were washed with 5% aqueous sodium carbonate solution (2×20 ml), brine (2×20 ml), dried over magnesium sulfate and the solvent removed in vacuo. The resulting residue was purified by flash column chromatography to afford the title compound (54 mg, 0.13 mmol) as the free base. The free base was dissolved in dichloromethane and hydrogen chloride (2M solution in diethyl ether; 1.0 ml, 2.0 mmol) was added. The mixture was concentrated in vacuo to afford the title compound as a 1:1 hydrochloride salt. $^1$H NMR (400 MHz, CD$_3$OD): 0.95-1.12 (2H, m), 1.16-1.27 (3H, m), 1.45 (6H, t, J 7), 1.55-1.63 (2H, m), 1.63-1.8 (3H, m), 1.8-1.95 (1H, m), 3.28-3.32 (4H, m), 3.97 (3H, s), 4.3 (2H, d, J 7), 4.96 (2H, s), 6.79 (1H, d, J 8), 7.13 (1H, t, J 8), 7.95 (1H, s), 8.04 (1H, d, J 8); EsIMS: m/z 413.1 [M+H]$^+$.

EXAMPLE 8

The method of Example 7 was further used to prepare the following compounds:

8A: 1-(Cyclohexyl)methyl-7-methoxy-3-(5-{[bis-(2-methoxyethyl)amino]methyl}-[1,2,4]-thiadiazol-3-yl)-1H-indole, hydrochloride salt The title compound was prepared using bis-(2-methoxyethyl)amine instead of diethylamine. EsIMS: m/z 473.1 [M+H]$^+$.

8B: 1-(Cyclohexyl)methyl-7-methoxy-3-{5-[(pyrrolidin-1-yl)methyl]-[1,2,4]thiadiazol-3-yl}-1H-indole, hydrochloride salt The title compound was prepared using pyrrolidine instead of diethylamine. EsIMS: m/z 411.1 [M+H]$^+$, 342.0.

8C: 1-(Cyclohexyl)methyl-7-methoxy-3-{5-[(2-methylpiperidin-1-yl)methyl]-[1,2,4]thiadiazol-3-yl}-1H-indole, trifluoroacetic acid salt The title compound was prepared using 2-methylpiperidine instead of diethylamine. The free base was purified by semi-prep. HPLC [Method (i)] to afford the title compound as a 1:1 trifluoroacetic acid salt. EsIMS: m/z 439.3 [M+H]$^+$.

8D: 1-(Cyclohexyl)methyl-3-(5-{[N-(2-hydroxyethyl)-N-methylamino]methyl}-[1,2,4]-thiadiazol-3-yl)-7-methoxy-1H-indole, hydrochloride salt The title compound was prepared using (2-hydroxyethyl)methylamine instead of diethylamine. The free base was purified by semi-prep. HPLC [Method (i)] to afford the title compound as a 1:1 trifluoroacetic acid salt. EsIMS: m/z 415.3 [M+H]$^+$, 328.3.

8E: 1-(Cyclohexyl)methyl-7-methoxy-3-(5{[N-(2-methoxyethyl)-N-methylamino]methyl}-[1,2,4]-thiadiazol-3-yl)-1H-indole, hydrochloride salt The title compound was prepared using N-(2-methoxyethyl)-N-methylamine instead of diethylamine. EsIMS: m/z 429.4 [M+H]$^+$.

EXAMPLE 9

1-(Cyclohexyl)methyl-3-{5-[1-(diethylamino)ethyl]-[1,2,4]thiadiazol-3-yl}-7-methoxy-1H-indole, hydrochloride salt To a cooled solution (dry-ice acetone bath) of 3-(1-cyclohexylmethyl-7-methoxy-1H-indol-3-yl)-[1,2,4]thiadiazole-5-carboxylic acid ethyl ester (500 mg, 1.3 mmol) in diethyl ether (50 ml) was added methyl magnesium bromide solution (0.52 ml, 3M in diethyl ether, 1.56 mmol) and the reaction stirred for 15 minutes, a further portion of methyl magnesium bromide solution (0.25 ml, 3M in diethyl ether, 0.75 mmol) was then added and the reaction mixture stirred for 5 minutes. The reaction was then quenched with saturated aqueous ammonium chloride (5 ml) and the reaction allowed to warm to room temperature. The reaction mixture was poured into a separating funnel and the organics washed with water (20 ml). The aqueous layer was then backwashed with diethyl ether (20 ml). The combined organic layers were dried over magnesium sulfate, filtered and the solvent removed in vacuo. The resulting residue was purified by flash column chromatography to give 1-[3-(1-cyclohexylmethyl-7-methoxy-1H-indol-3-yl)-[1,2,4]thiadiazol-5-yl]-ethanone (170 mg, 0.46 mmol) as a yellow solid.

To a solution of 1-[3-(1-cyclohexylmethyl-7-methoxy-1H-indol-3-yl)-[1,2,4]thiadiazol-5-yl]-ethanone (90 mg, 0.24 mmol) in acetonitrile (3 ml) was added diethylamine (0.248 ml, 2.4 mmol) and acetic acid (0.137 ml, 2.4 mmol) and the reaction mixture stirred for 30 minutes. To the reaction was added polymer supported cyanoborohydride (204 mg, loading 2.35 mmolg$^{-1}$, 0.48 mmol) and the reaction mixture subjected to microwave irradiation at 150° C. for 10 minutes. The reaction mixture was filtered through a 5 g Strata™ SCX giga tube. The tube was washed with methanol and then eluted with 2 M ammonia in methanol. The methanolic ammonia solution was evaporated and the resulting residue purified by flash column chromatography to give the title compound (62 mg, 0.145 mmol) as the free base. The free base was dissolved in dichloromethane (1 ml) and 2 M HCl in diethyl ether (1 ml, 2 mmol) added, the excess reagent and solvent were removed in vacuo to afford the title compound as a 1:1 hydrochloride salt. $^1$H NMR (400 MHz, CD$_3$OD): 1.0-1.2 (2H, m), 1.16-1.26 (3H, m), 1.38-1.5 (6H, m), 1.55-1.78 (5H, m), 1.82-1.94 (4H, m), 3.32-3.68 (4H, m), 3.97 (3H, s), 4.3 (2H, d, J 7.5), 5.36-5.48 (1H, m), 6.8 (1H, d, J 8), 7.14 (1H, t, J 7.5), 7.94 (1H, s), 8.02 (1H, d, J 8); EsIMS: m/z 427.4 [M+H]+, 328.4.

EXAMPLE 10

1-(Cyclohexyl)methyl-3-{5-[(diethylamino)methyl]-[1,2,4]-thiadiazol-3-yl}-7-fluoro-1H-indole, trifluoroacetic acid salt The title compound was prepared following the method of Example 7, using 1-(cyclohexyl)methyl-7-fluoro-1H-indole- 3-carboxylic acid amide (prepared from 7-fluoroindole) and using diethylamine. The free base was purified by semi-prep. HPLC [method (i)] to afford the title compound as a 1:1 trifluoroacetic acid salt. EsIMS: m/z 401.3 [M+H]$^+$.

EXAMPLE 11

7-Chloro-1-(cyclohexyl)methyl-3-{5-[(pyrrolidin-1-yl)methyl]-[1,2,4]thiadiazol-3-yl}-1H-indole, trifluoroacetic acid salt The title compound was prepared following the method of Example 7, using 7-chloro-1-(cyclohexyl)methyl-1H-indole-3-carboxylic acid amide (prepared from 7-chloroindole) and using pyrrolidine instead of diethylamine. The free base was purified by semi-prep. HPLC [method (i)] to afford the title compound as a 1:1 trifluoroacetic acid salt. EsIMS: m/z 417.3, 415.3 [M+H]$^+$.

EXAMPLE 12

1-(Cyclohexyl)methyl-7-ethyl-3-{5-[(pyrrolidin-1-yl)methyl]-[1,2,4]thiadiazol-3-yl}-1H-indole, trifluoroacetic acid salt The title compound was prepared using following the method of Example 7, using 1-(cyclohexyl)methyl-7-ethyl-1H-indole-3-carboxylic acid amide (prepared from 7-ethylindole) and using pyrrolidine instead of diethylamine. The free base was purified by semi-prep. HPLC [method (i)] to afford the title compound as a 1:1 trifluoroacetic acid salt. EsIMS: m/z 409.3 [M+H]$^+$

EXAMPLE 13

(R)-3-Cyclohexyl-6-{5-[(diethylamino)methyl]-[1,2,4]-thiadiazol-3-yl}-2,3-dihydropyrrolo[1,2,3-de]-1,4-benzoxazine, hydrochloride salt To a mixture of (R)-N-Boc-2-cyclohexylethanolamine (prepared as described for the (S) enantiomer, Luly et al., *J. Org. Chem.* 52, 1487-1492, 1987; 29.4 g, 94.5 mmol) and triphenylphosphine (37.2 g, 141.8 mmol) in toluene (150 ml) at 0° C. was added diisopropyl azodicarboxylate (19.5 ml, 99.2 mmol). After stirring for 1 h, 2-bromophenol (12.1 ml, 104.0 mmol) was added to the mixture at 0° C. The reaction mixture was stirred for 2 h at 0° C. and for 20 h at room temperature. The resulting mixture was partitioned between dichloromethane and water. The aqueous layer was extracted with dichloromethane and the combined organic layers were washed with 2 N sodium hydroxide solution and brine, dried over sodium sulfate and concentrated. The residue was purified by flash column chromatography eluting with 0-10% (v/v) ethyl acetate in heptane to afford (R)-2-(2-tert-butoxycarbonylamino-2-cyclohexylethoxy)bromobenzene (12.80 g, 32.1 mmol).

A mixture of (R)-2-(2-tert-butoxycarbonylamino-2-cyclohexylethoxy)bromobenzene (500 mg, 1.26 mmol), tetrakis (triphenylphosphine)palladium(0) (146 mg, 0.126 mmol) and sodium tert-butoxide (181 mg 1.88 mmol) in toluene (4.0 ml) was exposed to microwave irradiation for 10 min at 120° C. The resulting mixture was partitioned between dichloromethane and water. The aqueous layer was extracted with dichloromethane and combined organic layers were washed with brine, dried over sodium sulfate and concentrated. The residue was purified by flash column chromatography eluting with 0-17% (v/v) ethyl acetate in heptane to afford (R)-4-tert-butoxycarbonyl-3-cyclohexyl-3,4-dihydro-2H-1,4-benzoxazine (270 mg, 0.85 mmol). This reaction was repeated 13 times on the same scale to afford the same intermediate (a total of 3.98 g, 12.5 mmol).

A mixture of (R)-4-tert-butoxycarbonyl-3-cyclohexyl-3,4-dihydro-2H-1,4-benzoxazine (3.98 g, 12.5 mmol), 5 N hydrochloric acid (10 ml) and ethanol (10 ml) was stirred at 70° C. for 50 min. Ethanol was removed in vacuo and the residue was partitioned between dichloromethane and 2 N sodium hydroxide solution. The aqueous layer was extracted with dichloromethane and combined organic layers were washed with brine, dried over sodium sulfate and concentrated to afford (R)-3-cyclohexyl-3,4-dihydro-2H-1,4-benzoxazine (2.72 g, 12.5 mmol).

(R)-3-cyclohexyl-3,4-dihydro-2H-1,4-benzoxazine (2.72 g, 12.5 mmol) was dissolved in N,N-dimethylformamide (20 ml) and a solution of sodium nitrite (949 mg, 13.8 mmol) in water (3.0 ml) was added at 0° C. Then, 5 N hydrochloric acid (6.0 ml) was added at 0° C. The reaction mixture was stirred at 0° C. for 1 h, then partitioned between ethyl acetate and water. The aqueous layer was extracted with ethyl acetate and the combined organic layers were washed with brine, dried over sodium sulfate and concentrated. The obtained residue was dissolved in diethyl ether (50 ml), and lithium aluminum hydride in tetrahydrofuran (1.0 M; 9.51 ml, 9.51 mmol) was added at 0° C. The reaction mixture was stirred at 0° C. for 1 h, then quenched with ice water. Ethyl acetate was added to the mixture and the mixture was filtered through a plug of Celite, and the filter cake washed with ethyl acetate. The filtrate was partitioned and the aqueous layer extracted with ethyl acetate. The combined organic layers were washed with brine, dried over sodium sulfate and concentrated. The residue was purified by flash column chromatography eluting with 0-17% (v/v) ethyl acetate in heptane to afford (R)-4-amino-3-cyclohexyl-3,4-dihydro-2H-1,4-benzoxazine (1.47 g, 6.33 mmol).

Ethyl pyruvate (882 mg, 7.59 mmol) was added to a solution of (R)-4-amino-3-cyclohexyl-3,4-dihydro-2H-1,4-benzoxazine (1.47 g, 6.33 mmol) in ethanol (40 ml). The reaction mixture was stirred at room temperature for 15 min. To the reaction mixture, sulfuric acid (10% v/v in ethanol; 8.0 ml) was added. The reaction mixture was refluxed for 2 h. The mixture was cooled to room temperature and partitioned between ethyl acetate and sodium carbonate solution. The aqueous layer was extracted with ethyl acetate and the combined organic layers washed with brine, dried over sodium sulfate and concentrated. The residue was purified by flash column chromatography eluting with 0-10% (v/v) ethyl acetate in heptane to afford ethyl (R)-3-cyclohexyl-2,3-dihydropyrrolo[1,2,3-de]-1,4-benzoxazine-5-carboxylate (1.49 g, 4.76 mmol).

To a solution of ethyl (R)-3-cyclohexyl-2,3-dihydropyrrolo[1,2,3-de]-1,4-benzoxazine-5-carboxylate (1.49 g, 4.76 mmol) in ethanol (50 ml) was added 4 N sodium hydroxide (5.94 ml, 23.8 mmol). The mixture was stirred at 70° C. for 40 min. Ethanol was removed in vacuo, and the residue was neutralised with 2 N hydrochloric acid, and partitioned between dichloromethane and water. The aqueous layer was extracted with dichloromethane and the combined organic layers washed with brine, dried over sodium sulfate and concentrated. The residue was dissolved in quinoline (20 ml), then copper powder (453 mg, 7.13 mmol) was added. The mixture was stirred at 210° C. for 1 h. Ethyl acetate and water were added to the mixture at room temperature, and the mixture was filtered through a plug of Celite, and the filter cake washed with ethyl acetate. The filtrate was acidified with 5 N hydrochloric acid and partitioned. The aqueous layer was extracted with ethyl acetate and the combined organic layers washed with 1 N hydrochloric acid and brine, dried over sodium sulfate and concentrated. The residue was purified by flash column chromatography eluting with 0-10% (v/v) ethyl acetate in heptane to afford (R)-3-cyclohexyl-2,3-dihydropyrrolo[1,2,3-de]-1,4-benzoxazine (984 mg, 4.08 mmol).

To a solution of (R)-3-cyclohexyl-2,3-dihydropyrrolo[1,2,3-de]-1,4-benzoxazine (600 mg, 2.49 mmol) in N,N-dimethylformamide (5.0 ml) at 0° C. was added trifluoroacetic anhydride (0.311 ml, 2.73 mmol). The mixture was stirred at room temperature for 5 h, then partitioned between dichloromethane and water. The aqueous layer was extracted with dichloromethane, and combined organic layers were washed with brine, dried over $Na_2SO_4$ and concentrated. The residue was purified by flash chromatography eluting with 0-25% (v/v) ethyl acetate in heptane to afford (R)-3-cyclohexyl-6-trifluoromethylcarbonyl-2,3-dihydropyrrolo[1,2,3-de]-1,4-benzoxazine (628 mg, 1.86 mmol).

To a solution of (R)-3-cyclohexyl-6-trifluoromethylcarbonyl-2,3-dihydropyrrolo[1,2,3-de]-1,4-benzoxazine (628 mg, 1.86 mmol) in 1,4-dioxane (20 ml) was added 4 N NaOH (5.0 ml). The mixture was refluxed for 42 h, then acidified to pH 1 using 5 N hydrochloric acid and partitioned between dichloromethane and water. The aqueous layer was extracted with dichloromethane, and combined organic layers were washed with brine, dried over $Na_2SO_4$ and concentrated to afford (R)-3-cyclohexyl-2,3-dihydropyrrolo[1,2,3-de]-1,4-benzoxazine-6-carboxylic acid (572 mg). The title compound was prepared following the method of Example 7, using (R)-3-cyclohexyl-2,3-dihydropyrrolo[1,2,3-de]-1,4-benzoxazine-6-carboxylic acid amide (prepared from (R)-3-cyclohexyl-2,3-dihydropyrrolo[1,2,3-de]-1,4-benzoxazine-6-carboxylic acid) instead of 1-(cyclohexyl)methyl-7-methoxy-1H-indole-3-carboxylic acid amide. EsIMS: m/z 411.0 [M+H]$^+$; $[\alpha]_D^{22}$ –30.7° (c=1.50 mg/ml in chloroform)

EXAMPLE 14

The following compounds were prepared following the method of Example 7, using 7-fluoro-1-(tetrahydropyran-4-yl)methyl-1H-indole-3-carboxylic acid amide instead of 1-(cyclohexyl)methyl-7-methoxy-1H-indole-3-carboxylic acid amide. 7-fluoro-1-(tetrahydropyran-4-yl)methyl-1H-indole-3-carboxylic acid amide was prepared following the method of Example 1, using 7-fluoroindole instead of 7-methoxyindole and toluene-4-sulfonic acid tetrahydropyran-4-ylmethyl ester instead of cyclohexylmethyl bromide.

Method for Synthesis of the toluene-4-sulfonic Acid tetrahydropyran-4-ylmethyl Ester Intermediate p-Toluenesulfonyl chloride (29.8 g, 157 mmol) was added portionwise to a mixture of tetrahydro-2H-pyran-4-yl-methanol (20.0 g, 172 mmol) and pyridine (25.2 mL, 313 mmol) in dichloromethane (200 ml). The mixture was stirred at room temperature for 17 h, then quenched with aqueous hydrochloric acid (2 M; 100 ml). The layers were separated and the aqueous layer extracted with dichloromethane (2×100 ml). The organic layers were combined and concentrated in vacuo. Recrystallisation from dichloromethane: heptane (5:1) afforded toluene-4-sulfonic acid tetrahydro-pyran-4yl-methyl ester. The mother liquors were further purified by silica gel column chromatography eluting with 50% dichloromethane in n-heptane to yield a further quantity of toluene-4-sulfonic acid tetrahydro-pyran-4yl-methyl ester (total yield 41.6 g, 154 mmol).

14A: 3-{5-[(diethylamino)methyl]-[1,2,4]-thiadiazol-3-yl}-7-fluoro-1-(tetrahydropyran-4-yl)methyl-1H-indole, hydrochloride salt The title compound was prepared using diethylamine. EsIMS: m/z 403.1 [M+H]$^+$.

14B: 7-fluoro-3-{5-[(pyrrolidin-1-yl)methyl]-[1,2,4]-thiadiazol-3-yl}1-(tetrahydropyran-4-yl)methyl-1H-indole, hydrochloride salt The title compound was prepared using pyrrolidine instead of diethylamine.
EsIMS: m/z 401.0 [M+H]$^+$.

14C: 3-{5-[(dimethylamino)methyl]-[1,2,4]-thiadiazol-3-yl}-7-fluoro-1-(tetrahydropyran-4-yl)methyl-1H-indole, hydrochloride salt The title compound was prepared using dimethylamine instead of diethylamine.
EsIMS: m/z 375.0 [M+H]$^+$.

EXAMPLE 15

The following compounds were prepared following the method of Example 7, using 7-chloro-1-(tetrahydropyran-4-yl)methyl-1H-indole-3-carboxylic acid amide instead of 1-(cyclohexyl)methyl-7-methoxy-1H-indole-3-carboxylic acid amide. 7-chloro-1-(tetrahydropyran-4-yl)methyl-1H-indole-3-carboxylic acid amide was prepared following the method of Example 1, using 7-chloroindole instead of 7-methoxyindole and toluene-4-sulfonic acid tetrahydropyran-4-ylmethyl ester instead of cyclohexylmethyl bromide.

15A: 7-chloro-3-(5-{[N-ethyl-N-(2-methoxyethyl)amino]methyl}-[1,2,4]-thiadiazol-3-yl)-1-(tetrahydropyran-4-yl)methyl-1H-indole, hydrochloride salt The title compound was prepared using N-ethyl-N-(2-methoxyethyl)amine instead of diethylamine. EsIMS: m/z 451.0, 449.0 [M+H]$^+$.

15B: 7-chloro-3-{5-[(Pyrrolidin-1-yl)methyl]-[1,2,4]-thiadiazol-3-yl}1-(tetrahydropyran-4-yl)methyl-1H-indole, hydrochloride salt The title compound was prepared using pyrrolidine instead of diethylamine. EsIMS: m/z 419.3, 417.3 [M+H]$^+$.

15C: 7-chloro-3-(5-{[N-ethyl-N-(2-hydroxyethyl)amino]methyl}-[1,2,4]-thiadiazol-3-yl)-1-(tetrahydropyran-4-yl)methyl-1H-indole The title compound was prepared using N-ethyl-N-(2-hydroxyethyl)amine instead of diethylamine. EsIMS: m/z 437.1, 435.1 [M+H]$^+$.

EXAMPLE 16

1-(Cyclohexyl)methyl-7-methoxy-3-(4-{[N-(2-methoxyethyl)-N-methylamino]methyl}-[1,3]-thiazol-2-yl)-1H-indole, hydrochloride salt A mixture of 1-(cyclohexyl)methyl-7-methoxy-1H-indole-3-carboxylic acid amide (prepared from 7-methoxyindole as described in Example 1; 5.10 g, 17.8 mmol), Lawesson's reagent (7.92 g, 19.6 mmol), and toluene (150 ml) was stirred at room temperature for 4 days. The reaction mixture was concentrated in vacuo and the obtained reside was purified by column chromatography eluting with dichloromethane to afford 1-(cyclohexyl)methyl-7-methoxy-1H-indole-3-carbothioic acid amide (3.58 g). A mixture of 1-(cyclohexyl)methyl-7-methoxy-1H-indole-3-carbothioic acid amide (200 mg, 0.66 mmol), 1,3-dichloroacetone (126 mg, 0.99 mmol), and ethanol (2.0 ml) was stirred at 60° C. for 1 h. The reaction mixture was concentrated in vacuo, and the obtained residue was mixed with 5% aqueous sodium carbonate (100 ml). The resulting mixture was extracted with dichloromethane (4×100 ml). The organic layers were combined, washed with brine, dried over magnesium sulfate, and concentrated in vacuo. The obtained residue was purified by column chromatography eluting with 25% (v/v) ethyl acetate in n-heptane to give 3-[4-(chloromethyl)thiazol-2-yl]-1-(cyclohexyl)methyl-7-methoxy-1H-indole (200 mg).

A mixture of 3-[4-(chloromethyl)thiazol-2-yl]-1-(cyclohexyl)methyl-7-methoxy-1H-indole (100 mg, 0.27 mmol), (2-methoxyethyl)methylamine (119 mg, 1.33 mmol), 1,4-dioxane (2 ml), and acetonitrile (1 ml) was subjected to microwave irradiation for 10 min at 160° C. The reaction mixture was concentrated in vacuo and the obtained reside was mixed with aqueous sodium hydroxide (1M; 50 ml) and extracted with dichloromethane (4×50 ml). The combined organic layers were washed with brine, dried over magnesium sulfate, and concentrated in vacuo. The obtained residue was purified by column chromatography eluting with ethyl acetate to give the free base of the title compound as an oil. Hydrochloride salt formation was achieved by the addition of hydrogen chloride (1M solution in diethyl ether; 3 ml) to a solution of the free base in diethyl ether (15 ml). The mixture was concentrated in vacuo to afford the title compound as a 1:1 hydrochloride salt (95.1 mg). $^1$H NMR (400 MHz, CD$_3$OD) δ 1.00-1.30 (5H, m), 1.55-1.94 (6H, m), 3.00 (3H, s), 3.32-3.66 (5H, m), 3.80 (2H, t, J 5.0), 3.97 (3H, s), 4.29 (2H, d, J 7.2), 4.52 (2H, s), 6.81 (1H, d, J 8.0), 7.16 (1H, dd, J 8.0, 8.0), 7.62 (1H, s), 7.80 (1H, d, J 8.0), 7.85 (1H, s).
EsIMS: m/z 428.1 [M+H]$^+$, 339.0.

EXAMPLE 17

The method of Example 16 was further used to prepare the following compounds using alternative amines instead of (2-methoxyethyl)methylamine.

17A: 1-(Cyclohexyl)methyl-7-methoxy-3-{4-[(morpholin-4-yl)methyl]-[1,3]-thiazol-2-yl}-1H-indole, hydrochloride salt The title compound was prepared using morpholine instead of (2-methoxyethyl)-methylamine. EsIMS: m/z 426.3 [M+H]$^+$, 339.1.

17B: 1-(Cyclohexyl)methyl-3-{4-[(4-hydroxypiperidin-1-yl)methyl]-[1,3]-thiazol-2-yl}-7-methoxy-1H-indole, hydrochloride salt The title compound was prepared using 4-hydroxypiperidine instead of (2-methoxyethyl)methylamine. EsIMS: m/z 440.1 [M+H]$^+$, 399.0.

17C: 1-(Cyclohexyl)methyl-3-(4-{[N-isopropyl-N-(2-methoxyethyl)amino]methyl}-[1,3]-thiazol-2-yl)-7-methoxy-1H-indole, hydrochloride salt The title compound was prepared using N-isopropyl-N-(2-methoxyethyl)amine instead of (2-methoxyethyl)methylamine. EsIMS: m/z 456.4 [M+H]$^+$, 339.1.

17D: (S)-1-(Cyclohexyl)methyl-3-{4-[(2-hydroxymethyloyrrolidin-1-yl)methyl]-[1,3]-thiazol-2-yl}-7-methoxy-1H-indole The title compound was prepared using (S)-(+)-prolinol instead of (2-methoxyethyl)methylamine and isolated as the free base.
EsIMS: m/z 440.1 [M+H]$^+$, 339.1; [α]$_D^{22}$–10.0° (c=0.65 mg/ml in chloroform).

17E: 1-(Cyclohexyl)methyl-7-methoxy-3-{4-[(thiomorpholin-4-yl)methyl]-[1,3]-thiazol-2-yl}-1H-indole, hydrochloride salt The title compound was prepared using thiomorpholine instead of (2-methoxyethyl)methylamine. EsIMS: m/z 442.0 [M+H]$^+$, 339.0.

EXAMPLE 18

1-(Cyclohexyl)methyl-7-methoxy-3-{4-[1-(pyrrolidin-1-yl)ethyl]-[1,3]-thiazol-2-yl}-1H-indole, hydrochloride salt A solution of 1-chloro-2,3-butanedione (0.717 g, 5.95 mmol) in ethanol (3 ml) was added dropwise to a solution of 1-(cyclohexyl)methyl-7-methoxy-1H-indole-3-carbothioic acid amide (prepared as in Example 16; 1.20 g, 3.97 mmol) in ethanol (12 ml) at room temperature, and then the resulting mixture was stirred at room temperature for 3 days. The reaction mixture was concentrated in vacuo and the obtained residue was mixed with dichloromethane (50 ml) and washed sequentially with water and brine, dried over magnesium sulfate and concentrated in vacuo. The obtained residue was purified by column chromatography eluting with 33% (v/v) ethyl acetate in n-heptane to afford 1-{2-[1-(cyclohexyl)methyl-7-methoxy-1H-indol-3-yl]thiazol-4-yl}ethanone as a brown solid (1.11 g).

A mixture of 1-{2-[1-(cyclohexyl)methyl-7-methoxy-1H-indol-3-yl]thiazol-4-yl}ethanone (100 mg, 0.27 mmol), pyrrolidine (193 mg, 2.71 mmol), acetic acid (163 mg, 2.71 mmol) and acetonitrile (3 ml) was stirred at room temperature for 2 h. Macroporous triethylammonium methylpolystyrene cyanoborohydride (MP-cyanoborohydride, loading: 2.35 mmol/g, 231 mg, 0.543 mmol) was added and the resulting mixture was subjected to microwave irradiation at 130° C. for 10 min. The resin was removed by filtration, washing with dichloromethane and the filtrate concentrated in vacuo. The obtained residue was mixed with aqueous sodium hydroxide (1M; 100 ml) and extracted with dichloromethane (4×100 ml). The organic layers were combined, then washed with brine, dried over magnesium sulfate and concentrated in vacuo. The obtained residue was purified by column chromatography eluting with 5% methanol in ethyl acetate. The obtained oil was dissolved in diethyl ether (10 ml), then hydrochloric acid (1M solution in diethyl ether; 3 ml) was added to the solution. The resulting mixture was concentrated in vacuo to afford the title compound as a 1:1 hydrochloride salt (30.1 mg). $^1$H NMR (400 MHz, CD$_3$OD) δ; 0.98-1.32 (5H, m), 1.54-2.22 (13H, m), 3.22-3.44 (3H, m), 3.66-3.84 (1H, m), 3.97 (3H, s), 4.29 (2H, d, J 7.2), 4.60-4.72 (1H, m), 6.81 (1H, d, J 7.6), 7.15 (1H, dd, J 7.6, 8.0), 7.51 (1H, s), 7.79-7.90 (2H, m). EsIMS: m/z 424.1 [M+H]$^+$, 353.1.

EXAMPLE 19

1-(Cyclohexyl)methyl-7-fluoro-3-(4-{[N-isopropyl-N-(2-methoxyethyl)amino]methyl}-[1,3]-thiazol-2-yl)-1H-indole, trifluoroacetic acid salt The title compound was prepared following the method of Example 16, using 1-(cyclohexyl)methyl-7-fluoro-1H-indole-3-carboxylic acid amide (prepared from 7-fluoroindole) and N-isopropyl-N-(2-methoxyethyl)amine. The free base was purified by semi-prep. HPLC [method (i)] to afford the title compound as a 1:1 trifluoroacetic acid salt. EsIMS: m/z 444.3 [M+H]$^+$, 327.3.

EXAMPLE 19A 1-(Cyclohexyl)methyl-6-fluoro-3-[4-(diethylamino)methyl]-[1,3]-thiazol-2-yl)-1H-indole, trifluoroacetic acid salt The title compound was prepared following the method of Example 16, using 1-(cyclohexyl)methyl-6-fluoro-1H-indole-3-carboxylic acid amide (prepared from 6-fluoroindole) and diethylamine. The free base was purified by semi-prep. HPLC [method (i)] to afford the title compound as a 1:1 trifluoroacetic acid salt. EsIMS: m/z 400.1 [M+H]$^+$, 327.1.

EXAMPLE 20

7-Chloro-1-(cyclohexyl)methyl-3-(4-{[N-isopropyl-N-(2-methoxyethyl)amino]methyl}-[1,3]-thiazol-2-yl)-1H-indole, hydrochloride salt The title compound was prepared following the method of Example 16, using 7-chloro-1-(cyclohexyl)methyl-1H-indole-3-carboxylic acid amide (prepared from 7-chloroindole) and N-isopropyl-N-(2-methoxyethyl)amine. EsIMS: m/z 462.3, 460.3 [M+H]$^+$, 343.1.

EXAMPLE 21

1-(Cyclohexyl)methyl-7-ethyl-3-(4-{[N-isopropyl-N-(2-methoxyethyl)amino]methyl}-[1,3]-thiazol-2-yl)-1H-indole, trifluoroacetic acid salt The title compound was prepared following the method of Example 16, using 1-(cyclohexyl)methyl-7-ethyl-1H-indole-3-carboxylic acid amide (prepared from 7-ethylindole) and N-isopropyl-N-(2-methoxyethyl)amine. The free base was purified by semi-prep. HPLC [method (i)] to afford the title compound as a 1:1 trifluoroacetic acid salt. EsIMS: m/z 454.5 [M+H]$^+$, 337.3.

EXAMPLE 22

The following compounds were prepared following the method of Example 16 using (R)-3-cyclohexyl-2,3-dihydropyrrolo[1,2,3-de]-1,4-benzoxazine-6-carboxylic acid amide (prepared from (R)-3-cyclohexyl-2,3-dihydropyrrolo[1,2,3-de]-1,4-benzoxazine-6-carboxylic acid, described in Example 13) instead of 1-(cyclohexyl)methyl-7-methoxy-1H-indole-3-carboxylic acid amide.

22A: (R)-3-Cyclohexyl-6-{4-[(diethylamino)methyl]-[1,3]-thiazol-2-yl}-2,3-dihydropyrrolo-[1,2,3-de]-1,4-benzoxazine, hydrochloride salt The title compound was prepared using diethylamine instead of (2-methoxyethyl)methylamine. EsIMS: m/z 410.3 [M+H]$^+$, 337.3; $[\alpha]_D^{22}$ –37.5° (c=1.30 mg/ml in chloroform).

22B: (R)-3-Cyclohexyl-6-{4-[(N-ethyl-N-isopropylamino)methyl]-[1,3]-thiazol-2-yl}-2,3-dihydropyrrolo-[1,2,3-de]-1,4-benzoxazine, trifluoroacetic acid salt The title compound was prepared using N-ethyl-N-isopropylamine instead of (2-methoxyethyl)methylamine. The free base was purified by semi-prep. HPLC [method (i)] to afford the title compound as a 1:1 trifluoroacetic acid salt. EsIMS: m/z 424.3 [M+H]$^+$, 337.3; $[\alpha]_D^{22}$ –27.4° (c=1.25 mg/ml in chloroform)

22C: (R)-3-Cyclohexyl-6-{4-[(pyrrolidin-1-yl)methyl]-[1,3]-thiazol-2-yl}-2,3-dihydropyrrolo-[1,2,3-de]-1,4-benzoxazine, trifluoroacetic acid salt The title compound was prepared using pyrrolidine instead of (2-methoxyethyl)-methylamine. The free base was purified by semi-prep. HPLC [method (i)] to afford the title compound as a 1:1 trifluoroacetic acid salt. EsIMS: m/z 408.3 [M+H]$^+$, 337.3; $[\alpha]_D^{22}$32.6° (c=2.15 mg/ml in chloroform).

22D: (R)-3-Cyclohexyl-6-(4-{[N-isopropyl-N-(2-methoxyethyl)amino]methyl}-[1,3]-thiazol-2-yl)-2,3-dihydropyrrolo-[1,2,3-de]-1,4-benzoxazine, trifluoroacetic acid salt The title compound was prepared using N-isopropyl-N-(2-methoxyethyl)amine instead of (2-methoxyethyl)methylamine. The free base was purified by semi-prep. HPLC [method (i)] to afford the title compound as a 1:1 trifluoroacetic acid salt. EsIMS: m/z 454.3 [M+H]$^+$, 337.3; $[\alpha]_D^2$–58.4° (c=2.09 mg/ml in methanol).

22E: (R)-3-Cyclohexyl-6-(4-{[bis-(2-methoxyethyl)amino]methyl}-[1,3]-thiazol-2-yl)-2,3-dihydropyrrolo-[1,2,3-de]-1,4-benzoxazine, trifluoroacetic acid salt The title compound was prepared using bis-(2-methoxyethyl)amine instead of (2-methoxyethyl)methylamine. The free base was purified by semi-prep. HPLC [method (i)] to afford the title compound as a 1:1 trifluoroacetic acid salt. EsIMS: m/z 470.3 [M+H]$^+$, 337.3; $[\alpha]_D^{22}$–28.5° (c=1.20 mg/ml in chloroform).

EXAMPLE 23

The following compounds were prepared following the method of Example 16, using 7-chloro-1-(tetrahydropyran-4-yl)methyl-1H-indole-3-carboxylic acid amide instead of 1-(cyclohexyl)methyl-7-methoxy-1H-indole-3-carboxylic acid amide. 7-chloro-1-(tetrahydropyran-4-yl)methyl-1H-indole-3-carboxylic acid amide was prepared following the method of Example 1, using 7-chloroindole instead of 7-methoxyindole and toluene-4-sulfonic acid tetrahydropyran-4-ylmethyl ester (prepared as described in Example 14) instead of cyclohexylmethyl bromide.

23A: 7-chloro-3-{4-[(diethylamino)methyl]-[1,3-]-thiazol-2-yl}-1-(tetrahydropyran-4-yl)methyl-1H-indole, hydrochloride salt The title compound was prepared using diethylamine. EIMS: m/z 420.0, 418.4 [M+H]$^+$, 347.0, 345.0.

23B: 7-Chloro-3-(4-{[N-(2-hydroxyethyl)-N-isopropylamino]methyl}-1,3-thiazol-2-yl)-1-(tetrahydropyran-4-yl)methyl-1H-indole The title compound was prepared using N-(2-hydroxyethyl)-N-isopropylamine. EIMS: m/z 448.4 [M+H]$^+$, 347.1, 345.1.

23C: 7-Chloro-3-(4-{[N-ethyl-N-(2-hydroxyethyl)amino]methyl}-[1,3]-thiazol-2-yl)-1-(tetrahydropyran-4-yl)methyl-1H-indole The title compound was prepared using N-ethyl-N-(2-hydroxyethyl)amine. EIMS: m/z 436.3, 434.4 [M+H]$^+$, 347.0, 345.0.

23D: 7-Chloro-3-(4-{[N-(2-methoxyethyl)-N-methylamino]methyl}-[1,3]-thiazol-2-yl)-1-(tetrahydropyran-4-yl)methyl-1H-indole, hydrochloride salt The title compound was prepared using N-(2-methoxyethyl)-N-methylamine. EIMS: m/z 436.1, 434.1 [M+H]$^+$, 347.0, 345.0.

EXAMPLE 24

1-(cyclohexyl)methyl-3-{4-[(dimethylamino)methyl]-5-ethyl-[1,3]-thiazol-2-yl}-7-methoxy-1H-indole, hydrochloride salt Sodium ethoxide (0.68 g, 9.94 mmol) was added portionwise to a mixture of ethyldichloroacetate (1.22 ml, 9.94 mmol) and diethyl ether (10 ml) under ice-water cooling and the resulting mixture was stirred at 0° C. for 30 minutes. Propionaldehyde (0.79 ml, 10.93 mmol) was then added and the reaction mixture allowed to warm to room temperature slowly and stirring continued for 72 hours. The reaction mixture was then poured onto water (10 ml) and extracted with diethyl ether (2×15 ml). The organic layers were combined, dried over magnesium sulfate, and concentrated in vacuo to yield crude 3-chloro-2-oxo-pentanoic acid ethyl ester (1.8 g) which was used in the next step without further purification.

A mixture of 1-(cyclohexyl)methyl-7-methoxy-1H-indole-3-carbothioic acid amide (0.227 g, 0.754 mmol) and crude 3-chloro-2-oxo-pentanoic acid ethyl ester (1.34 g, 7.52 mmol) in dimethylformamide (4 ml) was subjected to microwave irradiation for 25 min at 140° C. The reaction mixture was concentrated in vacuo and the obtained reside was purified by silica gel column chromatography eluting with 25% acetone in heptane to afford crude 2-(1-cyclohexylmethyl-7- methoxy-1H-indol-3-yl)-5-ethyl-thiazole-4-carboxylic acid ethyl ester (0.490 g). This material was used in the next step without further purification.

Lithium borohydride (200 mg, 9.09 mmol) was added portionwise to a mixture of 2-(1-cyclohexylmethyl-7-methoxy-1H-indol-3-yl)-5-ethyl-thiazole-4-carboxylic acid ethyl ester (490 mg, 1.15 mmol) and tetrahydrofuran (5 ml) under ice-water cooling and the resulting mixture was stirred at 0° C. for 2 h. The reaction mixture was quenched with aqueous hydrochloric acid (2 M; 2 ml), and the aqueous layer extracted with dichloromethane (2×100 ml). The organic layers were combined, dried over magnesium sulfate, and concentrated in vacuo to yield the crude product. Silica gel column chromatography eluting with 66% ethyl acetate in heptane gave crude [2-(1-cyclohexylmethyl-7-methoxy-1H-indol-3-yl)-5-ethyl-thiazole-4-yl]-methanol (210 mg). This material was used in the next step without further purification. Methanesulfonylchloride (90 µl, 1.16 mmol) was added to a mixture of [2-(1-cyclohexylmethyl-7-methoxy-1H-indol-3-yl)-5-ethyl-thiazole-4-yl]-methanol (210 mg, 0.547 mmol), diisopropylethylamine (150 µl, 0.91 mmol) and dichloromethane (5 ml) under ice-water cooling and the resulting mixture was allowed to warm to room temperature slowly. Stirring was continued for 22 hours. The reaction mixture was quenched with 5% aqueous sodium carbonate (2 ml), and the aqueous layer extracted with dichloromethane (2×10 ml). The organic layers were combined, dried over magnesium sulfate, and concentrated in vacuo to yield the crude product. Flash column chromatography eluting with 10% acetone in n-heptane afforded 3-(4-chloromethyl-5-ethyl-thiazol-2-yl)-1-cyclohexylmethyl-7-methoxy-1H-indole (109 mg). Dimethylamine (2.2 M solution in tetrahydrofuran; 0.50 ml) was added to a mixture of 3-(4-chloromethyl-5-ethyl-thiazol-2-yl)-1-cyclohexylmethyl-7-methoxy-1H-indole (38 mg, 0.095 mmol), potassium carbonate (16 mg, 0.113 mmol) and sodium iodide (14 mg, 0.095 mmol) in acetonitrile (2 ml). The mixture was subjected to microwave irradiation for 5 min at 160° C., then partitioned between dichloromethane (20 ml) and 5% aqueous sodium carbonate (5 ml). The aqueous layer was extracted with dichloromethane (10 ml) and the combined organic layers were dried over magnesium sulfate and concentrated in vacuo. The resulting oil was dissolved in diethyl ether, then hydrogen chloride (1M solution in diethyl ether; 3 ml) was added to the solution. The resulting mixture was concentrated in vacuo to afford the title compound as a 1:1 hydrochloride salt (40 mg, 0.089 mmol). $^1$H NMR (400 MHz, CD$_3$OD) δ 1.04-1.15 (2H, m), 1.16-1.30 (3H, m), 1.43 (3H, t, J 7.0), 1.55-1.78 (5H, m), 1.82-1.92 (1H, m), 3.05 (8H, m), 3.99 (3H, s), 4.33 (2H, d, J 7), 4.62 (2H, s), 6.91 (1H, d, J 8.0), 7.29 (1H, t, J 8.0), 7.62 (1H, d, J 8), 8.30 (1H, s). EIMS: m/z 412.3 [M+H]$^+$, 367.0.

EXAMPLE 25

1-(Cyclohexyl)methyl-3-{5-[(diethylamino)methyl]-4-methyl-[1,3]-thiazol-2-yl}-7-methoxy-1H-indole, hydrochloride salt To a solution of 1-(cyclohexyl)methyl-7-methoxy-1H-indole-3-carbothioic acid amide (604 mg, 2.00 mmol) in EtOH (5.0 ml) was added ethyl 2-chloro-3-oxobutanoate (0.332 ml, 2.40 mmol). The mixture was refluxed for 1 h. After cooling to 0° C., the precipitate was collected by filtration to afford 1-cyclohexylmethyl-3-(5-ethoxycarbonyl-4-methylthiazol-2-yl)-7-methoxy-1H-indole (505 mg, 1.22 mmol).

To a solution of 1-cyclohexylmethyl-3-(5-ethoxycarbonyl-4-methylthiazol-2-yl)-7-methoxy-1H-indole (680 mg, 1.65 mmol) in THF (20 ml) was added lithium aluminium hydride (125 mg, 3.30 mmol) at 0° C. The mixture was stirred at 0° C. for 1 h, then quenched with ice water and extracted with dichloromethane. The combined organic layers were washed with brine, dried over sodium sulfate and concentrated. The residue was purified by flash chromatography eluting with 25-50% (v/v) ethyl acetate in heptane then 10% (v/v) methanol in dichloromethane to afford 1-cyclohexylmethyl-3-(5-hydroxymethyl-4-methylthiazol-2-yl)-7-methoxy-1H-indole (532 mg, 1.44 mmol). To a solution of 1-cyclohexylmethyl-3-(5-hydroxymethyl-4-methylthiazol-2-yl)-7-methoxy-1H-indole (74 mg, 0.20 mmol) and triethylamine (26 mg, 0.26 mmol) in dichloromethane (1.0 ml), was added methanesulfonyl chloride (28 mg, 0.24 mmol). The mixture was stirred at room temperature for 40 min. and partitioned between dichloromethane and 5% aqueous sodium hydrogen carbonate. The aqueous layer was extracted with dichloromethane, then combined organic layers were washed with brine, dried over sodium sulfate and concentrated to afford crude 1-cyclohexylmethyl-3-(5-methanesulfonyloxymethyl-4-methylthiazol-2-yl)-7-methoxy-1H-indole (65 mg, 0.15 mmol). A mixture of crude 1-cyclohexylmethyl-3-(5-methanesulfonyloxymethyl-4-methylthiazol-2-yl)-7-methoxy-1H-indole (64 mg, 0.14 mmol), potassium carbonate (29 mg, 0.21 mmol), sodium iodide (31 mg, 0.21 mmol) and diethylamine (21 mg, 0.28 mmol) in THF (1.5 ml) and acetonitrile (1.5 ml) was subjected to microwave irradiation for 5 min at 160° C. The resulting mixture was partitioned between dichloromethane and water. The aqueous layer was extracted with dichloromethane and combined organic layers were washed with brine, dried over sodium sulfate and concentrated. The residue was purified by flash chromatography eluting with 50-100% (v/v) ethyl acetate in heptane to afford 1-cyclohexylmethyl-3-(5-diethylaminomethyl-4-methylthiazol-2-yl)-7-methoxy-1H-indole (27 mg, 0.064 mmol). Hydrochloride salt formation was achieved by the addition of hydrogen chloride (1M solution in diethyl ether; 1 ml) to a solution of the free base in diethyl ether (1 ml) and ethanol (2 ml). The solvent was removed in vacuo and the precipitate was dried to afford title compound as a 1:1 hydrochloride salt (26 mg, 0.056 mmol). $^1$H NMR (400 MHz, DMSO-d$_6$) δ 0.95-1.25 (5H, m), 1.29 (6H, t, J 7.2), 1.40-1.52 (2H, m), 1.55-1.70 (3H, m), 1.72-1.84 (1H, m), 3.10-3.25 (4H, m), 3.93 (3H, s), 4.27 (2H, d, J 7.0), 4.56 (2H, d, J 5.0), 6.82 (1H, d, J 7.6), 7.14 (1H, t, J 7.6), 7.72 (1H, d, J 7.6), 8.00 (1H, s), 9.90 (1H, br s); EsIMS: m/z 426.3 [M+H]$^+$, 353.1.

EXAMPLE 26

1-(Cyclohexyl)methyl-3-{2-[(diethylamino)methyl]-[1,3]-thiazol-4-yl}-7-methoxy-1H-indole, hydrochloride salt To a solution of 7-methoxyindole (5.00 g, 34.0 mmol) in dimethylformamide (50 ml) under nitrogen was added sodium hydride (60% dispersion in mineral oil; 1.50 g, 37.4 mmol). The mixture was stirred at room temperature for 10 minutes before the addition of bromomethylcyclohexane (5.20 ml, 37.4 mmol). The resulting mixture was stirred at room temperature for 42 hours and then partitioned between ethyl acetate (150 ml) and water (150 ml). The aqueous layer was extracted with ethyl acetate (150 ml) and the combined organic layers were washed with brine (150 ml), dried over sodium sulfate and concentrated in vacuo. The crude intermediate was purified by flash column chromatography eluting with 0-10% (v/v) ethyl acetate in n-heptane to afford 1-(cyclohexyl)methyl-7-methoxy-1H-indole (7.48 g, 30.7 mmol). Chloroacetyl chloride (8.66 ml, 109 mmol) was added dropwise over a period of 1.5 h, to a stirred solution of pyridine (2.20 ml, 27.2 mmol) and 1-(cyclohexyl)methyl-7-methoxy-1H-indole (6.60 g, 27.2 mmol) in toluene (50 ml) at 55° C. The resulting mixture was heated at 55° C. for a further 0.5 h then allowed to cool to room temperature. Water (60 ml) and methanol (10 ml) were added. The organic layer was separated and concentrated under reduced pressure to afford a dark brown residue. The residue was purified by column chromatography eluting with 5% (v/v) ethyl acetate in n-heptane. The solid obtained was repeatedly recrystallised from ether to give 2-chloro-1-[1-(cyclohexyl)methyl-7-methoxy-1H-indol-3-yl]ethanone as a white solid (1.40 g).

2-Chloro-1-[1-(cyclohexyl)methyl-7-methoxy-1H-indol-3-yl]ethanone (0.73 g, 2.30 mmol) and 2-(tert-butylcarbonyloxy)thioacetamide (1.21 g, 6.89 mmol) were suspended in ethanol (10 ml) and the resulting mixture subjected to microwave irradiation at 150° C. for 10 min using an Emrys™ Optimizer EXP. The reaction mixture was concentrated in vacuo and the residue obtained was purified by flash column chromatography eluting with 5% (v/v) ethyl acetate in n-heptane to afford 1-(cyclohexyl)methyl-7-methoxy-3-{2-[(tert-butylcarbonyloxy)methyl]thiazol-4-yl}-1H-indole as a yellow oil (1.01 g).

1-(cyclohexyl)methyl-7-methoxy-3-{2-[(tertbutylcarbonyloxy)methyl]thiazol-4-yl}-1H-indole (0.92 g, 2.10 mmol) was dissolved in methanol (20 ml) and 4N sodium hydroxide (5 ml) added. The solution was stirred at room temperature for 2 h. The reaction mixture was concentrated in vacuo and the residue taken up in dichloromethane. Water (10 ml) was added and the organic layer separated. The aqueous layer was extracted with dichloromethane and the combined organic layers concentrated in vacuo to yield 1-(cyclohexyl)methyl-3-[2-(hydroxymethyl)thiazol-4-yl]-7-methoxy-1H-indole as a pale orange foam (0.55 g).

Methanesulfonyl chloride (174 µl, 2.25 mmol) was added to a solution of 1-(cyclohexyl)methyl-3-[2-(hydroxymethyl)thiazol-4-yl]7-methoxy-1H-indole (0.40 g, 1.12 mmol) and pyridine (182 µl, 2.25 mmol) in dichloromethane (8 ml). The resulting mixture was stirred at room temperature overnight. Further methanesulfonyl chloride (87 µl, 1.12 mmol) was added and stirring continued for 0.5 h. The mixture was concentrated in vacuo and the resulting orange residue was purified by flash column chromatography eluting with dichloromethane to afford 3-[2-(chloromethyl)thiazol-4-yl]-1-(cyclohexyl)methyl-7-methoxy-1H-indole as a yellow oil (0.415 g). 3-[2-(Chloromethyl)thiazol-4-yl]-1-(cyclohexyl)methyl-7-methoxy-1H-indole (0.08 g, 0.214 mmol) and diethylamine (221 µl, 2.14 mmol) were dissolved in acetonitrile (2 ml). The resulting mixture was exposed to microwave irradiation at 100° C. for 5 min. The mixture was concentrated in vacuo and the resulting residue was purified by column chromatography eluting with 33% (v/v) ethyl acetate in n-heptane. The resulting product was taken up in diethyl ether and hydrogen chloride (1M solution in diethyl ether; 1 ml) was added. The solution was concentrated in vacuo and the resulting solid triturated with ether, then dried to afford the title compound as a 1:1 hydrochloride salt (0.034 g). $^1$H NMR (400 MHz, CD$_3$OD) δ 0.99-1.25 (5H, m), 1.43 (6H, t, J 7.5), 1.56-1.90 (6H, m), 3.35-3.42 (4H, m), 3.96 (3H, s), 4.27 (2H, d, J 7.5), 4.75-4.80 (2H, s, masked by H$_2$O peak), 6.75 (1H, d, J 8.0), 7.08 (1H, dd, J 8.0, 8.0), 7.64-7.68 (3H, m). EsIMS: m/z 412.1 [M+H]$^+$, 339.0.

EXAMPLE 27

1-(Cyclohexyl)methyl-7-methoxy-3-{2-[(pyrrolidin-1-yl)methyl]-[1,3]-thiazol-4-yl}-1H-indole, hydrochloride salt The title compound was prepared following the method of Example 26, using pyrrolidine instead of diethylamine. EsIMS: m/z 410.3 [M+H]$^+$, 339.1.

EXAMPLE 28

1-(Cyclohexyl)methyl-3-{2-[(dimethylamino)methyl]-[1,3]-thiazol-5-yl}-7-methoxy-1H-indole, hydrochloride salt To a suspension of 1-cyclohexylmethyl-7-methoxy-1H-indole-3-carboxylic acid (5 g, 17.4 mmol) in dichloromethane (100 ml) was added oxalyl chloride (3.04 ml, 34.8 mmol) and the resulting solution stirred overnight. Excess solvent and reagent were then removed by evaporation. To the resulting residue was added copper (I) cyanide (6.2 g, 69.6 mmol), toluene (200 ml) and acetonitrile (10 ml) and the resulting reaction mixture heated at reflux for 7 hours. A further portion of copper (I) cyanide (1.6 g, 17.9 mmol) was then added and the reaction mixture heated at reflux overnight. The reaction mixture was cooled and filtered through a pad of dicalite. The dicalite was washed with acetonitrile and the combined filtrate evaporated to leave a red solid. The solid was purified by flash column chromatography eluting with 50% (v/v) dichloromethane in heptane to afford (1-cyclohexylmethyl-7-methoxy-1H-indol-3-yl)-oxoacetonitrile (4.7 g, 14.7 mmol).

To a solution of (1-cyclohexylmethyl-7-methoxy-1H-indol-3-yl)-oxoacetonitrile (975 mg, 3.29 mmol) in acetic acid (40 ml) under nitrogen was added 10% palladium on charcoal (90 mg). The reaction was placed under a hydrogen atmosphere and stirred for 14 h. The reaction mixture was then filtered through a pad of dicalite. The dicalite was washed with acetic acid and the combined filtrate evaporated to leave a red oil. The red oil was taken up in dichloromethane (50 ml) and to this was added methylchlorooxoacetate (0.393 ml, 4.28 mmol) followed by N-ethyldiisopropylamine (1.7 ml, 9.87 mmol) dropwise. The reaction was stirred for 1 h and poured into a separating funnel. The organics were washed sequentially with 2M aqueous hydrochloric acid (50 ml), 5% aqueous sodium carbonate (50 ml) and brine (50 ml). The organics were dried over sodium sulfate, filtered and the solvent removed in vacuo to leave a brown oil. The oil was purified by flash chromatography using dichloromethane followed by 66% (v/v) diethyl ether in heptane to afford N-[(1-cyclohexylmethyl-7-methoxy-1H-indol-3-yl)-2-oxo-ethyl] oxalamic acid methyl ester (573 mg, 1.48 mmol) as a yellow/brown solid.

To a solution of N-[(1-cyclohexylmethyl-7-methoxy-1H-indol-3-yl)-2-oxo-ethyl]-oxalamic acid methyl ester (429 mg, 1.11 mmol) in chloroform (20 ml) was added phosphorus pentasulfide (538 mg, 1.21 mmol) and the reaction mixture heated at reflux for 3.5 h. The reaction mixture was cooled, poured into a separating funnel and washed with water and then brine. The organic layers were then dried over magnesium sulfate, filtered and the solvent removed in vacuo. The resulting solid was purified by flash column chromatography eluting with dichloromethane to give 5-(1-cyclohexylmethyl-7-methoxy-1H-indol-3-yl)thiazole-2-carboxylic acid methyl ester (418 mg, 1.09 mmol) as a brown solid.

To a solution of 5-(1-cyclohexylmethyl-7-methoxy-1H-indol-3-yl)thiazole-2-carboxylic acid methyl ester (418 mg, 1.09 mmol) in methanol (10 ml) and tetrahydrofuran (10 ml) was added sodium borohydride (83 mg, 2.18 mmol) portionwise over 2 minutes. The reaction was stirred for a further 1 h and then quenched with aqueous hydrochloric acid (1M; 10 ml). The mixture was poured into a separating funnel, diluted with dichloromethane (50 ml) and washed with water (20 ml). The combined organic layers were dried, filtered and the solvent removed in vacuo to leave a yellow oil. The oil was purified by flash column chromatography using 50-100% (v/v) diethyl ether in heptane to give [5-(1-cyclohexylmethyl-7-methoxy-1H-indol-3-yl)thiazol-2-yl]-methanol (308 mg, 0.86 mmol) as an off-white foam.

To a solution of [5-(1-cyclohexylmethyl-7-methoxy-1H-indol-3-yl)thiazol-2-yl]methanol (308 mg, 0.86 mmol) in dichloromethane (20 ml) was added methanesulfonyl chloride (80 µl, 1.03 mmol) followed by triethylamine (0.156 ml, 1.12 mmol). The reaction was stirred for 30 minutes, then poured into a separating funnel, washed with 5% aqueous sodium carbonate, then brine and dried over magnesium sulfate. The solvent was removed in vacuo to afford methanesulfonic acid 5-(1-cyclohexylmethyl-7-methoxy-1H-indol-3-yl)-thiazol-2-yl methyl ester (411 mg, 0.94 mmol). To a solution of methanesulfonic acid 5-(1-cyclohexylmethyl-7-methoxy-1H-indol-3-yl)-thiazol-2-yl methyl ester (93 mg, 0.215 mmol) in tetrahydrofuran (2 ml) was added dimethylamine (2 M in tetrahydrofuran; 1 ml, 2 mmol) and the reaction mixture exposed to microwave irradiation at 150° C. for 15 minutes. The reaction mixture was diluted with dichloromethane (40 ml) and washed with a 1:1 (v/v) mixture of brine and saturated sodium bicarbonate, dried over magnesium sulfate, filtered and the solvent removed in vacuo. The resulting oil was purified by flash column chromatography to afford the title compound (70 mg, 0.18 mmol) as the free base. The free base was dissolved in dichloromethane (5 ml), hydrogen chloride (2 M solution in diethyl ether; 1 ml, 2 mmol) was added and the solvent removed in vacuo to afford the title compound as a 1:1 hydrochloride salt.
$^1$H NMR (400 MHz, $CD_3OD$): 0.96-1.12 (2H, m), 1.13-1.26 (3H, m), 1.5-1.62 (2H, m), 1.62-1.78 (3H, m), 1.78-1.92 (1H, m), 3.01 (6H, s), 3.96 (3H, s), 4.26 (2H, d, J 5.5), 4.71 (2H, s), 6.78 (1H, d, J 8.0), 7.11 (1H, t, J 8.0), 7.41 (1H, d, J 8.0), 7.52 (1H, s), 8.08 (1H, s); EsIMS: m/z 384.0 [M+H]$^+$, 339.0, 243.1.

EXAMPLE 29

1-(Cyclohexyl)methyl-3-{4-[(diethylamino)methyl]-[1,3]-oxazol-2-yl}-7-methoxy-1H-indole, hydrochloride salt To a solution of 1-cyclohexylmethyl-7-methoxy-1H-indole-3-carboxylic acid amide (500 mg, 1.75 mmol) in toluene (4 ml) was added 1,3-dichloroacetone (333 mg, 2.62 mmol) and the reaction mixture subjected to microwave irradiation at 150° C. for 30 minutes. The resulting black solution was diluted with dichloromethane (50 ml) and washed with 5% aqueous sodium carbonate solution (5×20 ml), dried over magnesium sulfate, filtered and the solvent removed in vacuo. The resulting brown oil was purified by flash column chromatography using 5% (v/v) acetone in petroleum ether 40-60 to give 3-(4-chloromethyl-oxazol-2-yl)-1-cyclohexylmethyl-7-methoxy-1H-indole (510 mg, 1.42 mmol) as a white solid.

To a solution of 3-(4-chloromethyl-oxazol-2-yl)-1-cyclohexylmethyl-7-methoxy-1H-indole (100 mg, 0.28 mmol) in tetrahydrofuran (1 ml) was added diethylamine (0.29 ml, 2.8 mmol) and the reaction mixture subjected to microwave irradiation at 150° C. for 15 minutes. The reaction mixture was poured into a separating funnel, diluted with dichloromethane (40 ml) and washed with 5% aqueous sodium carbonate solution (2×25 ml), brine (20 ml), dried over magnesium sulfate and the solvent evaporated in vacuo to leave an orange oil. The oil was purified by flash column chromatography using 10% (v/v) methanol in dichloromethane to give the title compound (92 mg, 0.23 mmol) as the free base. The free base was dissolved in dichloromethane and hydrogen chloride (1M solution in diethyl ether; 2 ml, 2 mmol) was added. The mixture was concentrated in vacuo to afford the title compound as a 1:1 hydrochloride salt. $^1$H NMR (400 MHz, $CD_3OD$): 0.97-1.28 (5H, m), 1.44 (6H, t, J 7.0), 1.5-1.8 (5H, m), 1.8-1.95 (1H, m), 3.3-3.5 (4H, m), 3.97 (3H, s), 4.29 (2H, d, J 7.0), 4.38 (2H, s), 6.8 (1H, d, J 8.0), 7.2 (1H, t, J 8.0), 7.8 (1H, s), 7.82 (1H, s), 8.2 (1H, s); EsIMS: m/z 396.0 [M+H]$^+$, 323.4, 295.4, 268.3.

EXAMPLE 30

1-(Cyclohexyl)methyl-7-methoxy-3-{5-[(pyrrolidin-1-yl)methyl]-[1,3]-oxazol-2-yl}-1H-indole, trifluoroacetic acid salt A mixture of 1-cyclohexylmethyl-7-methoxy-1H-indole-3-carboxylic acid amide (563 mg, 1.97 mmol), 2-chloro-3-oxo-propionic acid methyl ester (Gangjee et al., *J. Med. Chem.* 44, 1993-2003, 2001; 1.48 g, 9.85 mmol) and dimethylacetamide (10 ml) was subjected to microwave irradiation at 90° C. for 2×5 minutes using an Emrys™ Optimizer EXP. The reaction mixture was diluted with dichloromethane (150 ml), then washed with 5% aqueous magnesium sulfate (2×100 ml) and brine (150 ml). The organic extracts were dried over magnesium sulfate and concentrated in vacuo. The resulting residue was purified by flash column chromatography eluting with 25% (v/v) ethyl acetate in heptane to afford an inseparable mixture of 2-(1-cyclohexylmethyl-7-methoxy-1H-indol-3-yl)-oxazole-5-carboxylic acid methyl ester and 1-cyclohexylmethyl-7-methoxy-3-oxazol-2-yl-1H-indole (87:13 ratio by HPLC; 0.613 g). Lithium aluminum hydride solution (1M solution in diethyl ether; 2.88 ml, 2.88 mmol) was added dropwise to a mixture of 2-(1-cyclohexylmethyl-7-methoxy-1H-indol-3-yl)-oxazole-5-carboxylic acid methyl ester and 1-cyclohexylmethyl-7-methoxy-3-oxazol-2-yl-1H-indole (557 mg) dissolved in tetrahydrofuran (10 ml) under ice-methanol cooling. The resulting mixture was stirred for 30 minutes at 0° C., then diluted with diethyl ether (40 ml). Excess sodium sulfate decahydrate was then added and the resulting mixture stirred at room temperature for 18 h. The mixture was filtered through a pad of dicalite and washed with diethyl ether (100 ml); the filtrate was then concentrated in vacuo. The resulting residue was purified by column chromatography eluting with 50% ethyl acetate in n-heptane to afford [2-(1-cyclohexylmethyl-7-methoxy-1H-indol-3-yl)-oxazol-5-yl]-methanol as a yellow solid (242 mg, 0.71 mmol). Methanesulfonyl chloride (98 mg, 0.85 mmol) was added dropwise to a solution of [2-(1-cyclohexylmethyl-7-methoxy-1H-indol-3-yl)-oxazol-5-yl]-methanol (242 mg, 0.71 mmol) dissolved in dichloromethane (15 ml) under ice-methanol cooling, then triethylamine (93 mg, 0.92 mmol) was added dropwise, cooling was then removed and the mixture stirred for 16 h. The mixture was then diluted with dichloromethane (30 ml), washed with saturated sodium carbonate solution (30 ml) in a hydrophobic frit tube. The organic extracts were dried over magnesium sulfate, then concentrated in vacuo. A mixture of the resulting residue (110 mg, 0.26 mmol), pyrrolidine (185 mg, 2.60 mmol) and tetrahydrofuran (2.5 ml) was subjected to microwave irradiation at 150° C. for 15 minutes. The resulting mixture was concentrated in vacuo and purified by flash column chromatography (2% (v/v) ammonia in methanol/dichloromethane in 1:49 ratio as eluant) to give a brown gum. The gum was further purified by semi-prep. HPLC [Method (i)] to furnish 1-cyclohexylmethyl-7-methoxy-3-(5-pyrrolidin-1-ylmethyl-oxazol-2-yl)-1H-indole as a trifluoroacetic acid salt (14 mg). $^1$H NMR (400 MHz, CD$_3$OD) δ 0.99-1.27 (5H, m), 1.54-1.78 (5H, m), 1.86 (1H, m), 2.00-2.24 (4H, m), 3.25-3.44 (2H, m), 3.53-3.74 (2H, m), 3.97 (3H, s), 4.29 (2H, d, J 7.0), 4.64 (2H, s), 6.81 (1H, s, J 7.0), 7.15 (1H, t, J 8.0), 7.41 (1H, s), 7.79 (1H, d, J 7.5), 7.82 (1H, s). EsIMS: m/z 394.1 [M+H]$^+$, 323.1.

EXAMPLE 31

1-(Cyclohexyl)methyl-3-{5-[(diethylamino)methyl]-4-methyl-[1,3]-oxazol-2-yl}-7-methoxy-1H-indole, hydrochloride salt A mixture of 1-(cyclohexyl)methyl-7-methoxy-1H-indole-3-carboxylic acid amide (500 mg, 1.75 mmol), ethyl-2-chloroacetoacetate (2.88 g, 17.6 mmol) and dimethylformamide (10 ml) was subjected to microwave irradiation at 185° C. for 15 minutes using an Emrys™ Optimizer EXP. The reaction mixture was diluted with dichloromethane (100 ml), then washed with 5% aqueous magnesium sulfate (2×50 ml), water (50 ml) and brine (50 ml). The organic extracts were dried over magnesium sulfate and concentrated in vacuo. The resulting residue was purified by column chromatography eluting with 33% (v/v) dichloromethane in n-heptane to afford an inseparable mixture of 2-(1-cyclohexylmethyl-7-methoxy-1H-indol-3-yl)4-methyl-oxazole-5-carboxylic acid ethyl ester and 1-cyclohexylmethyl-7-methoxy-3-(4-methyl-oxazol-2-yl)-1H-indole (78:22 ratio by HPLC; 0.586 g). This reaction was repeated on the same scale.

Lithium aluminum hydride (1M solution in diethyl ether; 5.8 ml, 5.8 mmol) was added dropwise to a mixture of 2-(1-cyclohexylmethyl-7-methoxy-1H-indol-3-yl)-4-methyl-oxazole-5-carboxylic acid ethyl ester and 1-cyclohexylmethyl-7-methoxy-3-(4-methyl-oxazol-2-yl)-1H-indole (1171 mg) dissolved in tetrahydrofuran (20 ml) under ice-methanol cooling. The resulting mixture was stirred for 20 minutes at 0° C., then diluted with diethyl ether (40 ml). Excess sodium sulfate decahydrate was added and the resulting mixture was stirred at room temperature for 18 h. The mixture was filtered through a pad of dicalite, washing with diethyl ether (100 ml) and the filtrate concentrated in vacuo. The residue was purified by flash column chromatography eluting with 50% (v/v) ethyl acetate in n-heptane to afford [2-(1-cyclohexylmethyl-7-methoxy-1H-indol-3-yl)4-methyl-oxazol-5-yl]-methanol as a white solid (774 mg). Methane sulfonyl chloride (281 mg, 2.45 mmol) was added dropwise to a solution of [2-(1-cyclohexylmethyl-7-methoxy-1H-indol-3-yl)-4-methyl-oxazol-5-yl]-methanol (724 mg, 2.04 mmol) dissolved in dichloromethane (40 ml) at −78° C. under nitrogen. Triethylamine (269 mg, 2.66 mmol) was added dropwise and the mixture allowed to warm to room temperature with stirring for 2 h. The mixture was then diluted with dichloromethane (100 ml), washed with saturated sodium carbonate solution (2×100 ml) and brine (100 ml). The organic extracts were dried over magnesium sulfate then concentrated in vacuo. A mixture of the resulting residue (100 mg, 0.23 mmol), diethylamine (169 mg, 2.30 mmol) and tetrahydrofuran (2 ml) was subjected to microwave irradiation at 150° C. for 15 minutes. The resulting mixture was concentrated in vacuo and purified by flash column chromatography, eluting with 2% ammonia in methanol/dichloromethane in 1:49 ratio, to afford a brown gum. The gum was dissolved in dichloromethane (0.5 ml), then hydrogen chloride (1M solution in diethyl ether; 0.5 ml) was added and the mixture concentrated in vacuo to afford the title compound as a 1:1 hydrochloride salt (32 mg). $^1$H NMR (400 MHz, CD$_3$OD) δ 0.85-1.38 (6H, m), 1.46 (6H, t, J 7.5), 1.55-1.78 (4H, m), 1.88 (1H, m), 2.39 (3H, s), 3.34 (4H, q, J 7.6), 3.98 (3H, s), 4.34 (2H, d, J 6.9), 4.65 (2H, s), 6.88 (1H, d, J 8.2), 7.23 (1H, t, J 8.0), 7.74 (1H, d, J 8.0), 8.00 (1H, s). EsIMS: m/z 410.3 [M+H]$^+$, 337.1.

EXAMPLE 32

1-(Cyclohexyl)methyl-3-{2-[(diethylamino)methyl]-[1,3]-oxazol-5-yl}-7-methoxy-1H-indole, hydrochloride salt To a solution of (1-cyclohexylmethyl-7-methoxy-1H-indol-3-yl)-oxoacetonitrile (prepared as described in Example 28; 2.39 g, 8.06 mmol) in acetic acid (50 ml) under nitrogen was added 10% palladium on charcoal (240 mg). The reaction was placed under a hydrogen atmosphere and stirred overnight. The reaction mixture was then filtered through a pad of dicalite. The dicalite was washed with acetic acid and the combined filtrate evaporated to leave a red oil. The red oil was taken up in dichloromethane (50 ml) and to this was added chloroacetyl chloride (0.77 ml, 9.67 mmol) followed by triethylamine (3.4 ml, 24.2 mmol) dropwise. The reaction was stirred for 30 minutes and poured into a separating funnel. The organics were washed sequentially with 5% aqueous sodium carbonate (2×30 ml) and brine (30 ml). The organics were dried over magnesium sulfate, filtered and the solvent removed in vacuo to leave a red/brown oil. The oil was purified by flash chromatography using 20-100% (v/v) dichloromethane in heptane followed by 25-50% (v/v) diethyl ether in heptane to afford 2-chloro-N-[2-(1-cyclohexylmethyl-7-methoxy-1H-indol-3-yl)-2-oxoethyl]-acetamide (2.32 g, 6.1 mmol).

To a solution of 2-chloro-N-[2-(1-cyclohexylmethyl-7-methoxy-1H-indol-3-yl)-2-oxoethyl]-acetamide (200 mg, 0.53 mmol) in tetrahydrofuran (2 ml) was added diethylamine (0.55 ml, 5.3 mmol) and the reaction mixture subjected to microwave irradiation at 150° C. for 15 minutes. The reaction mixture was poured into a separating funnel and dichloromethane (30 ml) added. The organics were washed sequentially with 5% aqueous sodium carbonate and brine. The organics were dried over magnesium sulfate, filtered and the solvent removed in vacuo to give a brown solid. The brown solid was dissolved in tetrahydrofuran (2 ml) and (methoxycarbonylsulfamoyl)triethylammonium hydroxide, inner salt (505 mg, 2.12 mmol) added. The resulting reaction mixture was subjected to microwave irradiation at 150° C. for 15 minutes and quenched with methanol (20 ml). The solvent was removed in vacuo and the residue purified by flash chromatography using 50% (v/v) ethyl acetate in heptane, followed by semi-prep. HPLC [Method (ii)] to afford a white solid. The solid was dissolved in dichloromethane (~5 ml) and hydrogen chloride (1M solution in diethyl ether; 1 ml) added. The mixture was concentrated in vacuo to afford the title compound as a 1:1 hydrochloride salt (77 mg, 0.2 mmol). $^1$H NMR (400 MHz, CD$_3$OD) δ$_H$ 0.97-1.12 (2H, m), 1.15-1.25 (3H, m), 1.44 (6H, t, J 6.9), 1.52-1.62 (2H, m), 1.62-1.77 (3H, m), 1.77-1.9 (1H, m), 3.36 (4H, q, J 6.7), 3.95 (3H, s), 4.26 (2H, d, J 7), 4.64 (2H, s), 6.77 (1H, d, J 8), 7.11 (1H, t, J 8), 7.38 (1H, s), 7.41 (1H, d, J 8), 7.56 (1H, s); EsIMS: m/z 396.1 [M+H]$^+$, 323.4, 268.4.

EXAMPLE 33

1-(Cyclohexyl)methyl-3-(5-ethyl-5,6-dihydro-4H-pyrrolo[3,4-d]isothiazol-3-yl)-7-methoxy-1H-indole, hydrochloride salt To a suspension of 5-(1-Cyclohexylmethyl-7-methoxy-1H-indole)-[1,3,4]-oxathiazol-2-one (prepared as described in Example 7; 100 mg, 0.25 mmol) in m-xylene (0.5 ml) was added diethylacetylene dicarboxylate (0.2 ml, 1.25 mmol) and the reaction subjected to microwave irradiation at 200° C. for 5 minutes. The reaction mixture was then purified directly by flash column chromatography using 0-100% (v/v) dichloromethane in heptane to afford 3-(1-cyclohexylmethyl-7-methoxy-1H-indol-3-yl)-isothiazole-4,5-dicarboxylic acid diethyl ester (141 mg, 0.3 mmol). This reaction was repeated on a 1.255 mmol scale and the whole combined and purified by flash column chromatography using 50-60% (v/v) dichloromethane in heptane to give the same intermediate (882 mg, 1.87 mmol).

To a cooled solution (ice/methanol bath) of 3-(1-cyclohexylmethyl-7-methoxy-1H-indol-3-yl)-isothiazole-4,5-dicarboxylic acid diethyl ester (400 mg, 0.85 mmol) in tetrahydrofuran (20 ml) was added lithium aluminium hydride (1M solution in THF; 1.91 ml, 1.91 mmol) and the reaction mixture stirred for 20 minutes. To the reaction mixture was added excess sodium sulfate decahydrate and the reaction stirred vigorously for 1.5 hours. The resulting mixture was filtered through a pad of dicalite, washing with diethyl ether. The filtrate was concentrated in vacuo and the resulting oil purified by flash column chromatography to afford 3-(1-cyclohexylmethyl-7-methoxy-1H-indol-3-yl)-4-hydroxymethyl-isothiazol-5-yl]-methanol (141 mg, 0.3 mmol). To a solution of 3-(1-cyclohexylmethyl-7-methoxy-1H-indol-3-yl)-4-hydroxymethyl-isothiazol-5-yl]-methanol (194 mg, 0.5 mmol) in dichloromethane (10 ml) was added methanesulfonyl chloride (0.182 ml, 1.16 mmol) followed by triethylamine (0.175 ml, 1.26 mmol) and the reaction mixture stirred for 45 minutes. A further portion of methanesulfonyl chloride (0.07 ml, 0.44 mmol) and triethylamine (0.15 ml, 1 mmol) was added and the reaction stirred for a further 2 hours. The reaction mixture was poured into a separating funnel, washed with 5% aqueous sodium carbonate solution, then brine, dried over magnesium sulfate and the solvent evaporated in vacuo. The resulting residue was purified by flash column chromatography using 33%-100% (v/v) dichloromethane in heptane and then diethyl ether to afford methanesulfonic acid {4-chloromethyl-3-[1-(cyclohexyl)methyl-7-methoxy-1H-indol-3-yl]-isothiazol-5-yl}methyl ester (113 mg, 0.23 mmol).

To a solution of methanesulfonic acid {4-chloromethyl-3-[1-(cyclohexyl)methyl-7-methoxy-1H-indol-3-yl]-isothiazol-5-yl}methyl ester (90 mg, 0.19 mmol) in tetrahydrofuran (1 ml) was added ethylamine (0.186 ml, 0.37 mmol) and triethylamine (0.05 ml, 0.37 mmol) and the reaction mixture subjected to microwave irradiation at 150° C. for 15 minutes. The reaction mixture was poured into a separating funnel, diluted with dichloromethane (30 ml) and washed with 5% aqueous sodium carbonate solution (2×10 ml), brine (10 ml), dried over magnesium sulfate and the solvent removed in vacuo. The reaction was repeated on a 0.166 mmol scale to give the same intermediate. The crude products were combined and purified by flash column chromatography using ethyl acetate to give the title compound (36 mg, 0.09 mmol) as the free base. The free base was dissolved in dichloromethane and hydrogen chloride (2M solution in diethyl ether; 1 ml, 2 mmol) was added. The mixture was concentrated in vacuo to afford the title compound as a 1:1 hydrochloride salt. $^1$H NMR (400 MHz, CD$_3$OD): 0.97-1.15 (2H, m), 1.15-1.27 (3H, m), 1.47 (3H, t, J 7), 1.52-1.61 (2H, m), 1.62-1.77 (3H, m), 1.81-1.95 (1H, m), 3.63 (2H, q, J 7), 3.95 (3H, s), 4.28 (2H, d, J 7), 4.62-4.75 (2H, m), 4.95-5.12 (2H, m), 6.77 (1H, d, J 8), 7.09 (1H, t, J 8), 7.43 (1H, s), 8.01 (1H, d, J 8); EsIMS: m/z 396.0 [M+H]$^+$, 353.4, 351.3, 320.3.

EXAMPLE 34

1-(Cyclohexyl)methyl-7-methoxy-3-{5-[(pyrrolidin-1-yl)methyl]-isoxazol-3-yl}-1H-indole, trifluoroacetic acid salt Phosphorous oxychloride (12 ml, 0.13 mol) was added slowly over 30 minutes to dimethylformamide (30 ml) at −10° C. The solution was allowed to warm to 0° C. over 1 h, then 1-(cyclohexyl)methyl-7-methoxy-1H-indole (prepared as in Example 26; 3.2 g, 13 mmol) was added portionwise and the solution stirred at room temperature for 16 h. The solution was cooled in an ice bath and diluted with water, then neutralised carefully with sodium bicarbonate and extracted with ethyl acetate (3×50 ml). The organic extracts were combined and the solvent removed in vacuo. The residue (3.5 g) was dissolved in aqueous sodium hydroxide solution (5 M; 100 ml) and the mixture refluxed at 100° C. for a further 16 h. The solution was cooled and extracted with ethyl acetate (3×50 ml), the organic extracts combined and the solvent removed in vacuo to afford 1-(cyclohexyl)methyl-7-methoxy-1H-indole-3-carbaldehyde (2.2 g, 8.12 mmol) as a white solid.

To a solution of 1-(cyclohexyl)methyl-7-methoxy-1H-indole-3-carbaldehyde (780 mg, 2.9 mmol) in a mixture of ethanol (8 ml) and water (2 ml) was added hydroxylamine hydrochloride (403 mg, 5.8 mmol) and sodium acetate (713 mg, 8.7 mmol) and the solution stirred for 64 h at room temperature. The mixture was concentrated in vacuo and the residue diluted with water (50 ml) and extracted with ethyl acetate (3×50 ml). The product was recrystallised from diethyl ether/hexane to yield 1-cyclohexylmethyl-7-methoxy-1H-indole-3-carbaldehyde oxime (380 mg, 1.3 mmol) as a yellow powder.

To a solution of 1-cyclohexylmethyl-7-methoxy-1H-indole-3-carbaldehyde oxime (170 mg, 0.59 mmol) in dichloromethane (5 ml) cooled to 0° C., was added N-chlorosuccinimide (119 mg, 0.89 mmol) and the mixture allowed to warm to room temperature with stirring for 1 h. Propargyl bromide (8 µl, 0.65 mmol) and triethylamine (9 µl, 0.65 mmol) were added and the mixture stirred at room temperature for 16 h. The solvent was removed in vacuo and the residue was purified by flash column chromatography eluting with 60-80% (v/v) dichloromethane in n-heptane to afford 3-(5-bromomethyl-isoxazol-3-yl)-1-cyclohexylmethyl-7-methoxy-1H-indole (150 mg, 0.37 mmol) as a yellow solid.

To a solution of 3-(5-bromomethyl-isoxazol-3-yl)-1-cyclohexylmethyl-7-methoxy-1H-indole (120 mg, 0.31 mmol) in acetonitrile (3 ml), diethylamine (0.024 ml, 0.34 mmol) was added. The mixture was stirred at room temperature for 16 h. The mixture was filtered and the solvent removed in vacuo. The residue was purified using semi-prep. HPLC [Method (ii)] to afford the title compound as a trifluoroacetic acid salt (20 mg).

$^1$H NMR (400 MHz, CD$_3$OD) δ 1.03-1.09 (2H, m), 1.21 (3H, m), 1.57-1.74 (5H, m), 1.83-1.89 (1H, m), 2.14 (4H, m), 3.38-3.60 (4H, m), 3.96 (3H, s), 4.27-4.29 (2H, d, J 6.9), 4.69

(2H, s), 6.78 (1H, d, J 7.5), 7.02 (1H, s), 7.08-7.12 (1H, m), 7.67 (1H, s), 7.67-7.69 (1H, d, J 8.1). EsIMS: m/z 394.1 [M+H]$^+$, 323.4.

EXAMPLE 35

1-(Cyclohexyl)methyl-7-methoxy-3-(5-{[bis-(2-hydroxyethyl)amino]methyl}-isoxazol-3-yl)-1H-indole, trifluoroacetic acid salt The title compound was prepared following the method of Example 34 using diethanolamine instead of pyrrolidine. EsIMS: m/z 428.4 [M+H]$^+$, 323.4.

EXAMPLE 36

1-(Cyclohexyl)methyl-7-fluoro-3-{5-[(pyrrolidin-1-yl)methyl]-thiophen-2-yl)-1H-indole, hydrochloride salt To an ice cooled solution of 7-fluoroindole (2.0 g, 14.8 mmol) in dimethylformamide (50 ml) was added sodium hydride (60% dispersion in mineral oil; 0.88 g, 22.2 mmol) and the mixture stirred for 15 min before dropwise addition of benzenesulfonyl chloride (2.26 ml, 17.8 mmol). The mixture was then stirred at room temperature for 18 h.

The suspension was then diluted with water (200 ml), extracted with tert-butyl methyl ether (3×100 ml) and the combined organic layers washed with water (3×100 ml), dried with sodium sulfate and concentrated in vacuo. The residue was purified by flash column chromatography eluting with 20% (v/v) ethyl acetate in isohexane to afford 1-benzenesulfonyl-7-fluoroindole as a colourless solid (3.96 g, 14.4 mmol). To a solution of 1-benzenesulfonyl-7-fluoroindole (2.0 g, 7.27 mmol) in dimethylformamide (10 ml) was added a solution of bromine (0.75 ml, 14.55 mmol) in dimethylformamide (25 ml) dropwise over 3 min. The mixture was then stirred at room temperature for 10 min and poured onto a mixture of sodium metabisulphite (2 g), ammonium hydroxide solution (3 ml), water (100 ml) and crushed ice (100 g). The resulting suspension was stirred until all colour had discharged and extracted into tert-butyl methyl ether (2×100 ml). The combined organic layers were washed with water (2×100 ml), dried with sodium sulfate and the solvent removed in vacuo to afford 1-benzenesulfonyl-3-bromo-7-fluoroindole as a salmon coloured solid (2.35 g, 6.64 mmol).

A solution of 1-benzenesulfonyl-3-bromo-7-fluoroindole (0.5 g, 1.41 mmol), 5-formyl-2-thiophene boronic acid (0.24 g, 1.55 mmol), bis(triphenylphosphine) palladium (II) dichloride (0.06 g, 0.08 mmol) and triethylamine (0.39 ml, 2.82 mmol) in ethanol (4 ml) was subjected to microwave irradiation at 150° C. for 420 s. The resulting suspension was concentrated under reduced pressure and the residue passed through a silica pad eluting with dichloromethane to afford crude 5-(1-benzenesulfonyl-7-fluoroindol-3-yl)-thiophene-2-carboxaldehyde as a brown solid (0.42 g) which was used in the next step with no further purification.

To the crude 5-(1-benzenesulfonyl-7-fluoroindol-3-yl)-thiophene-2-carboxaldehyde was sequentially added 4 Å molecular sieves (1 g), pyrrolidine (0.44 ml, 5.36 mmol), sodium cyanoborohydride (0.034 g, 0.54 mmol) and glacial acetic acid (1 drop). The resulting mixture was then stirred at room temperature for 18 h, filtered and the filter cake washed with methanol (2×30 ml) and dichloromethane (2×30 ml). The combined filtrate was concentrated in vacuo, dissolved in dichloromethane (20 ml), washed with aqueous sodium hydroxide (2M; 15 ml), dried with sodium sulphate and concentrated in vacuo. The residue was then purified by flash column chromatography eluting with 0-10% (v/v) methanol in dichloromethane to afford 1-benzenesulfonyl-7-fluoro-3-(5-(5-pyrrolidin-1-ylmethyl-thiophen-2-yl)-indole as a yellow oil (0.22 g, 0.46 mmol).

1-benzenesulfonyl-7-fluoro-3-(5-pyrrolidin-1-ylmethyl-thiophen-2-yl)-indole (0.20 g, 0.46 mmol) and potassium carbonate (0.25 g, 1.82 mmol) were treated with a mixture of methanol and water (3:1 v/v; 4 ml) and subjected to microwave irradiation at 100° C. for 600 s. The resulting suspension was then concentrated under reduced pressure and partitioned between dichloromethane (10 ml) and water (10 ml). The organic phase was separated and the aqueous phase washed with dichloromethane (10 ml). The combined organic layers were dried with sodium sulfate and concentrated in vacuo. The residue was purified by flash column chromatography eluting with 0-10% (v/v) methanol in dichloromethane to afford 7-fluoro-3-(5-pyrrolidin-1-ylmethyl-thiophen-2-yl)-indole as a colourless solid (0.10 g, 0.35 mmol).

To a solution of 7-fluoro-3-(5-pyrrolidin-1-ylmethyl-thiophen-2-yl)-indole (0.10 g, 0.35 mmol) in dimethylformamide (3 ml) was added sodium hydride (60% dispersion in mineral oil; 0.03 g, 0.71 mmol) and the mixture stirred at room temperature for 15 minutes. Bromomethylcyclohexane (0.05 ml, 0.39 mmol) was added and the mixture stirred at 60° C. for 18 h. The suspension was then diluted with water (30 ml), extracted into tert-butyl methyl ether (2×30 ml), the combined organic layers washed with water (2×20 ml), dried with sodium sulfate and evaporated under reduced pressure. The residue was purified by flash chromatography eluting with 5% (v/v) dichloromethane in methanol to afford the title compound (free base) as a colourless solid (0.05 g, 0.13 mmol). This was dissolved in diethyl ether (3 ml) and treated with hydrogen chloride (1 M solution in diethyl ether) to give on evaporation the title compound (1:1 hydrochloride salt) as a colourless solid. $^1$H NMR (400 MHz, CD$_3$OD) $\delta_H$ 1.02-1.34 (5H, m), 1.57-1.93 (6H, m), 2.11-2.19 (4H, m), 3.38-3.57 (4H, m), 4.19 (2H, d, J 7.4), 4.65 (2H, s), 6.91-7.36 (4H, m), 7.58 (1H, s), 7.71 (1H, d, J 8.1);

EsIMS: m/z 396.9 [M+H]$^+$, 326.0

EXAMPLE 37

1-(Cyclohexyl)methyl-3-{5-[(diethylamino)methyl]-[1,3,4]-oxadiazol-2-yl}-7-methoxy-1H-indole, hydrochloride salt To a suspension of 1-cyclohexylmethyl-7-methoxy-1H-indole-3-carboxylic acid (1.0 g, 3.48 mmol) in dichloromethane (20 ml) was added oxalyl chloride (0.6 ml, 6.96 mmol) and the reaction stirred for 3.5 h. The solvent was evaporated under reduced pressure and the resulting residue redissolved in dichloromethane (20 ml). To the solution was added chloroacetic acid hydrazide (1.3 g, 8.97 mmol) and triethylamine (2.9 ml, 20.9 mmol) and the reaction mixture stirred for 4 h and then left to stand overnight. The solvent was evaporated under reduced pressure and the resulting residue purified by flash column chromatography eluting with 50-100% (v/v) ethyl acetate in heptane to give 1-cyclohexylmethyl-7-methoxy-1H-indole-3-carboxylic acid N'-(2-chloroacetyl)hydrazide (397 mg, 1.05 mmol).

To a solution of 1-cyclohexylmethyl-7-methoxy-1H-indole-3-carboxylic acid N'-(2-chloroacetyl)hydrazide (250 mg, 0.662 mmol) in tetrahydrofuran (3 ml) was added (methoxycarbonylsulfamoyl)triethylammonium hydroxide, inner salt (315 mg, 1.32 mmol) and the resulting reaction mixture subjected to microwave irradiation at 150° C. for 15 minutes. The reaction mixture was quenched with methanol and the solvent evaporated. The resulting residue was purified by flash chromatography using 33-50% (v/v) ethyl acetate in heptane to give 3-(5-chloromethyl-[1,3,4]oxadiazol-2-yl)-1-cyclohexylmethyl-7-methoxy-1H-indole (169 mg, 0.47 mmol) as a yellow solid. This reaction was repeated on a 0.53 mmol scale to afford the same intermediate (a total of 276 mg, 0.77 mmol).

To a solution of 3-(5-chloromethyl-[1,3,4]oxadiazol-2-yl)-1-cyclohexylmethyl-7-methoxy-1H-indole (92 mg, 0.26 mmol) in tetrahydrofuran (1 ml) was added diethylamine (0.134 ml, 1.28 mmol) and the reaction mixture subjected to microwave irradiation at 150° C. for 15 minutes. The resulting mixture was purified by flash column chromatography to afford the title compound (87 mg, 0.22 mmol) as the free base. The free base was dissolved in dichloromethane and hydrogen chloride (2M solution in diethyl ether; 1 ml, 2 mmol) was added. The excess reagent and solvent were removed by evaporation to the leave the title compound (1:1 hydrochloride salt) as a white solid. $^1$H NMR (400 MHz, CD$_3$OD): 0.97-1.12 (2H, m), 1.15-1.26 (3H, m), 1.46 (6H, t, J 7), 1.53-1.63 (2H, m), 1.63-1.78 (3H, m), 1.8-1.95 (1H, m), 3.44 (4H, q, J 7), 3.98 (3H, s), 4.33 (2H, d, J 7), 4.84 (2H, s), 6.85 (1H, d, J 7), 7.19 (1H, t, J 7.9), 7.73 (1H, d, J 8), 7.94 (1H, s); EsIMS: m/z 397.1 [M+H]$^+$, 324.4, 270.5.

EXAMPLE 38

1-(Cyclohexyl)methyl-7-methoxy-3-{5-[(pyrrolidin-1-yl)methyl]-[1,3,4]-thiadiazol-2-yl}-1H-indole, hydrochloride salt To a solution of 1-cyclohexylmethyl-7-methoxy-1H-indole-3-carboxylic acid N'-(2-chloroacetyl)hydrazide (prepared as described in Example 37; 50 mg, 0.139 mmol) in tetrahydrofuran (0.5 ml) was added phosphorus pentasulfide (62 mg, 0.139 mmol) and the reaction mixture subjected to microwave irradiation at 150° C. for 5 minutes. The reaction was repeated twice on a 0.7 mmol scale. The combined reaction mixture was poured into a separating funnel and diluted with dichloromethane (60 ml). The organics were washed with 5% aqueous sodium carbonate (2×30 ml), brine (30 ml), dried over sodium sulfate and the solvent removed in vacuo. The resulting residue was purified by flash column chromatography to afford 3-(5-chloromethyl-[1,3,4]thiadiazol-2-yl)-1-cyclohexylmethyl-7-methoxy-1H-indole (186 mg, 0.49 mmol).

To a solution of 3-(5-chloromethyl-[1,3,4]thiadiazol-2-yl)-1-cyclohexylmethyl-7-methoxy-1H-indole (93 mg, 0.25 mmol) in tetrahydrofuran was added pyrrolidine (0.101 ml, 1.235 mmol) and the mixture subjected to microwave irradiation at 150° C. for 5 minutes. The resulting reaction mixture was purified by flash column chromatography to give the title compound (42 mg, 0.1 mmol) as the free base. The free base was dissolved in dichloromethane and hydrogen chloride (1M solution in diethyl ether; 1 ml, 1 mmol) was added. The excess reagent and solvent were removed in vacuo to afford the title compound as a 1:1 hydrochloride salt.
$^1$H NMR (400 MHz, CDCl$_3$): 0.94-1.1 (2H, m), 1.13-1.23 (3H, m), 1.5-1.75 (8H, m), 1.8-1.9 (5H, m), 2.66-2.73 (4H, m), 3.95 (3H, s), 4.12 (2H, s), 4.23 (2H, d, J 7), 6.73 (1H, d, J 7.8), 7.17 (1H, t, J 8), 7.66 (1H, s), 7.77 (1H, d, J 8); EsIMS: m/z 411.1 [M+H]$^+$, 340.0, 324.4, 286.1, 270.5.

EXAMPLE 39

7-Chloro-3-{5-[(2,2-dimethyl-pyrolidin-1-yl)methyl]-[1,2,4]oxadiazol-3-yl}-1-(tetrahydropyran-4-yl)methyl-1H-indole, hydrochloride salt Method for the Synthesis of 2,2-dimethyl-pyrrolidinone:
Sodium borohydride (3.36 g, 89 mmol) was added portionwise to a stirred and cooled solution (0° C.) of NiCl$_2$.6H$_2$O in methanol (200 ml). The reaction mixture was stirred for 30 min before addition of methyl-4-methyl-4-nitropentanoate as solution in methanol (100 ml). The reaction temperature was maintained at 0° C. before the addition of sodium borohydride (7.86 g, 208 mmol) portionwise. The reaction was then left to stir for 72 hours, before filtration through a pad of celite. The resultant cake was washed with methanol (150 ml) and the filtrate evaporated to dryness. The resulting solid was triturated with dichloromethane (400 ml) and filtered through a pad of celite. After washing the cake with dichloromethane (200 ml) the filtrate was evaporated to give the product, 2,2-dimethyl-pyrrolidinone, as pale green gum (6.8 g).

Method for the Synthesis of 2,2-dimethyl-pyrrolidine hydrochloride:
Lithium aluminium hydride (1M solution in tetrahydrofuran; 120 ml, 120 mmol) was added slowly to a stirred solution of 2,2-dimethyl-pyrrolidinone (6 g, 53 mmol) in tetrahydrofuran (150 ml). Upon complete addition, the reaction was warmed to reflux, and stirred at reflux under argon for 16 hours. After this time, the reaction was allowed to cool to 0° C., before addition of water (2.2 ml), 10% sodium hydroxide solution (2.2 ml) and water (6.6 ml) at 45 minute intervals. The resultant slurry was diluted with diethyl ether (150 ml) and filtered through a pad of celite. The cake was washed with diethyl ether (250 ml) and the filtrate acidified with hydrochloric acid (1M solution in diethyl ether; 63 ml). The resultant yellow solid was filtered off to afford 2,2-dimethyl-pyrrolidine hydrochloride (4.8 g).

Method for the Synthesis of (2,2-dimethyl-pyrrolidin-1-yl)-acetic acid ethyl ester:
Ethylchloroacetate (0.15 ml, 1.37 mmol), potassium carbonate (416 mg, 1.5 mmol) and 2,2-dimethyl-pyrolidine (0.280 mg, 2.06 mmol) were suspended in ethanol (3 ml) and subjected to microwave irradiation at 120° C. for 45 min. The resultant mixture was suspended in diethyl ether (30 ml), extracted with 2M hydrochloric acid (30 ml) and the organic layer discarded. The aqueous layer was treated with a slight excess of 4N sodium hydroxide solution and extracted with diethyl ether (3×30 ml). The organic layers were combined, dried over sodium sulfate, filtered and solvent removed under reduced pressure to afford (2,2-dimethyl-pyrrolidin-1-yl)-acetic acid ethyl ester (156 mg).

The title compound was prepared following the method of Example 1 using 7-chloroindole instead of 7-methoxyindole; toluene-4-sulfonic acid tetrahydropyran-4-ylmethyl ester (prepared as described in Example 14) instead of cyclohexylmethyl bromide and (2,2-dimethyl-pyrrolidin-1-yl)-acetic acid ethyl ester instead of N,N-dimethylglycine methyl ester
$^1$H NMR (400 MHz, CD$_3$OD) δ 1.45 (10H, m), 2.22 (5H, m), 3.35 (2H, m), 3.59 (1H, br s), 3.91 (2H, d, J 11.1), 4.12 (1H, br s), 4.52 (2H, d, J 7.1), 4.71 (1H, br s), 4.95 (1H, br s), 7.23 (1H, t, J 7.6), 7.32 (1H, d, J 7.6), 8.08 (1H, s), 8.13 (1H, d, J 7.6). EsIMS: m/z 429.5 [M+H]$^+$.

EXAMPLE 40

1-(Cyclohexyl)methyl-3-{5-[(pyrrolidin-1-yl)methyl]-[1,2,4]thiadiazol-3-yl}-1H-indole-7-carbonitrile, hydrochloride salt A suspension of [3-(7-bromo-1-cyclohexylmethyl-1H-indol-3-yl)-[1,2,4]thiadiazol-5-yl]-methanol (prepared from 7-bromoindole as described in Example 7; 2×250 mg, 0.16 mmol), zinc (II) cyanide (2×72 mg, 0.61 mmol) and tetrakis(triphenylphosphine)-palladium(0) (2×21 mg, 18.3 μmol) in DMF (2×4 ml) was subjected to microwave irradiation at 200° C. for 5 min using an Emrys™ Optimizer EXP. The reactions were combined and poured into a separating funnel, to this was added dichloromethane (~50 ml). The organics were washed successively with water (2×20 ml), 1M aqueous HCl (20 ml) and brine (20 ml), dried over magnesium sulfate, filtered, and the solvent removed in vacuo. The resulting oil was purified by flash column chromatography eluting with 50-100% (v/v) dichloromethane in heptane and then diethyl ether to give 1-cyclohexylmethyl-3-(5-hydroxymethyl-[1,2,4]thiadiazol-3-yl)-1H-indole-7-carbonitrile (416 mg, 1.18 mmol) as a light yellow oil which crystallised on standing.

To a solution of 1-cyclohexylmethyl-3-(5-hydroxymethyl-[1,2,4]thiadiazol-3-yl)-1H-indole-7-carbonitrile (416 mg, 1.18 mmol) in dichloromethane (40 ml) was added methanesulfonyl chloride (0.110 ml, 1.42 mmol) and triethylamine (0.214 ml, 1.53 mmol) sequentially. The reaction was allowed to stir for 1 h and then poured into a separating funnel. The organics were washed with 2M aqueous sodium carbonate solution (20 ml), brine (20 ml), dried over magnesium sulfate, filtered, and the solvent removed in vacuo to afford methanesulfonic acid 3-(7-cyano-1-cyclohexylmethyl-1H-indol-3-yl)-[1,2,4]thiadiazol-5-ylmethyl ester (503 mg, 1.17 mmol) which was used without further purification.

To a solution of methanesulfonic acid 3-(7-cyano-1-cyclohexylmethyl-1H-indol-3-yl)-[1,2,4]thiadiazol-5-ylmethyl ester (120 mg, 0.28 mmol) in dichloromethane (3 ml) was added pyrrolidine (0.12 ml, 1.4 mmol) and the reaction subjected to microwave irradiation at 100° C. for 5 minutes. The reaction was purified directly by flash column chromatography eluting with dichloromethane then 25-50% (v/v) ethyl acetate in heptane to afford the title compound (71 mg, 0.175 mmol) as the free base. The free base (35 mg, 0.086 mmol) was dissolved in dichloromethane (2 ml) and hydrogen chloride (1M solution in diethyl ether) was added. The mixture was concentrated in vacuo to afford the title compound as a 1:1 hydrochloride salt. $^1$H NMR (400 MHz, $CD_3OD$): 1.06-1.36 (7H, m), 1.62-1.80 (5H, m), 1.91-2.07 (1H, m), 2.09-2.34 (2H, br m), 3.35-4.20 (4H, br m), 4.42 (2H, d, J 7), 5.07 (2H, s), 7.37 (1H, t, J 8), 7.69 (1H, dd, J 7, 1), 8.23 (1H, s); 8.84 (1H, dd, J 8, 1) EsIMS: m/z 406.4 $[M+H]^+$.

EXAMPLE 41

In-vitro Determination of Efficacy and Potency at the Human CB1 Receptor Expressed in CHO Cells Chinese Hamster Ovary (CHO) cells expressing the human CB1 receptor and a luciferase reporter gene were suspended in phenol red/serum free DMEM/F-12 nut mix containing penicillin/streptomycin (50 U/50 µg/ml) and fungizone (1 µg/ml) and seeded into 96 well plates at a density of $3\times10^4$ cells per well (100 µl final volume). Cells were incubated overnight (approx. 18 h at 37° C., 5% $CO_2$/95% air) prior to assay. The test compound (10 mM solution in dimethylsulfoxide) was diluted in F12 Nut Mix to give a range of stock solutions from 0.11 mM to 0.11 nM. The stock solutions (10 µl) were added directly to the relevant wells. The plates were incubated at 37° C. for 5 h to allow agonist-induced expression of the luciferase enzyme. Under subdued light, LucLite substrate (Packard; reconstituted as per manufacturer's instructions; 100 µl) was added to each well. Plates were covered with Top Seal and then incubated at room temperature for 5 minutes before counting on the Packard TopCount (single photon counting, 0.01 minute count time, 5 minute count delay).

A "best-fit" curve was fitted by a minimum sum of squares method to the plot of counts per second (CPS) against compound concentration (M) to obtain an $EC_{50}$ value. Table 1 shows the $pEC_{50}$ values obtained for some representative compounds of the invention.

TABLE 1

| Example | Chemical name | Chemical structure | $pEC_{50}$ |
|---|---|---|---|
| 2G | (R)-1-(Cyclohexyl)methyl-7-methoxy-3-[5-(1-methylpyrrolidin-2-yl)-[1,2,4]-oxadiazol-3-yl]-1H-indole, hydrochloride salt | 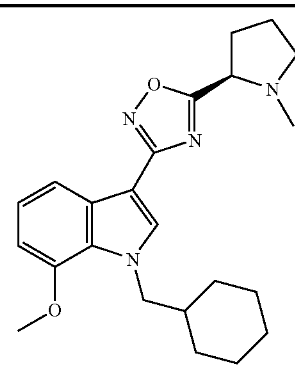 | 7.5 |
| 13 | (R)-3-Cyclohexyl-6-{5-[(diethylamino)methyl]-[1,2,4]-thiadiazol-3-yl}-2,3-dihydro-pyrrolo[1,2,3-de]-1-4-benzoxazine, hydrochloride salt | 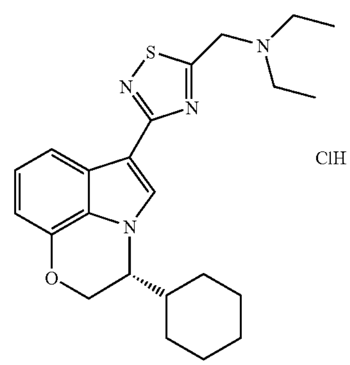 | 8.1 |

TABLE 1-continued

| Example | Chemical name | Chemical structure | pEC$_{50}$ |
|---|---|---|---|
| 14B | 7-fluoro-3-{5-[(pyrrolidin-1-yl)methyl]-[1,2,4]-thiadiazol-3-yl}-1-(tetrahydropyran-4-yl)methyl-1H-indole, hydrochloride salt | 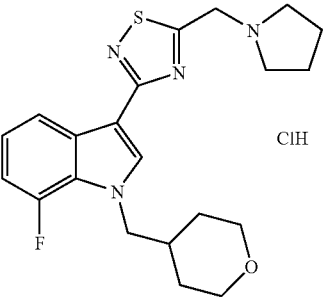 | 7.3 |
| 15A | 7-chloro-3-(5-{[N-ethyl-N-(2-methoxyethyl)amino]methyl}-[1,2,4]-thiadiazol-3-yl)-1-(tetrahydropyran-4-yl)methyl-1H-indole, hydrochloride salt | 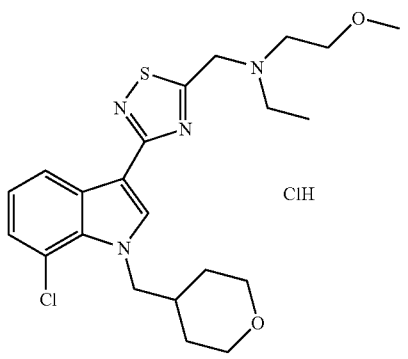 | 8.0 |
| 15B | 7-chloro-3-{5-[(pyrrolidin-1-yl)methyl]-[1,2,4]-thiadiazol-3-yl}-1-(tetrahydropyran-4-yl)methyl-1H-indole, hydrochloride salt | 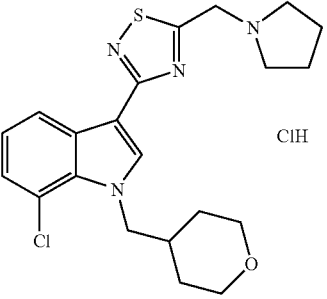 | 7.7 |
| 15C | 7-chloro-3-(5-{[N-ethyl-N-(2-hydroxyethyl)amino]methyl}-[1,2,4]-thiadiazol-3-yl)-1-(tetrahydropyran-4-yl)methyl-1H-indole | 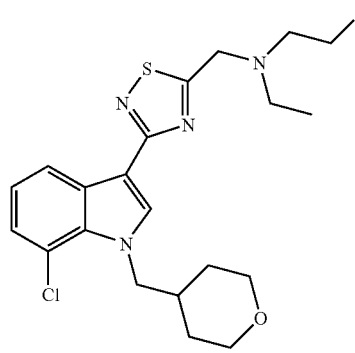 | 8.0 |

TABLE 1-continued

| Example | Chemical name | Chemical structure | pEC$_{50}$ |
|---|---|---|---|
| 20 | 7-Chloro-1-(cyclohexyl)methyl-3-(4-{[N-isopropyl-N-(2-methoxyethyl)amino]methyl}-[1,3]-thiazol-2-yl)-1H-indole, hydrochloride salt | 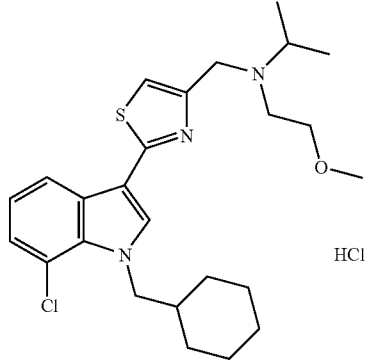 | 8.3 |
| 23B | 7-Chloro-3-(4-{[N-(2-hydroxyethyl)-N-isopropylamino]methyl}-[1,3]-thiazol-2-yl)-1-(tetrahydropyran-4-yl)methyl-1H-indole | 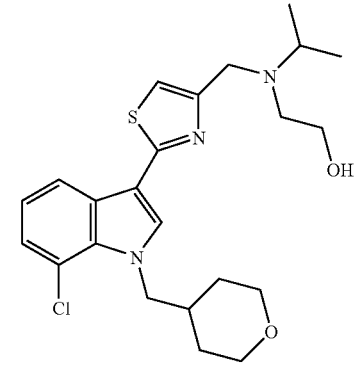 | 8.0 |
| 23C | 7-Chloro-3-(4-{[N-ethyl-N-(2-hydroxyethyl)amino]methyl}-[1,3]-thiazol-2-yl)-1-(tetrahydropyran-4-yl)methyl-1H-indole | 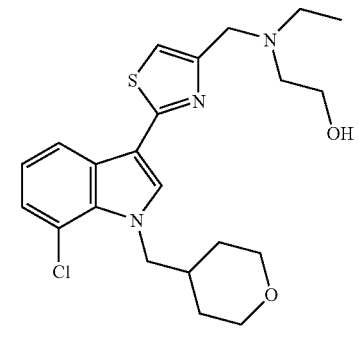 | 7.9 |
| 23D | 7-Chloro-3-(4-{[N-(2-methoxyethyl)-N-methylamino]methyl}-[1,3]-thiazol-2-yl)-1-(tetrahydropyran-4-yl)methyl-1H-indole, hydrochloride salt | 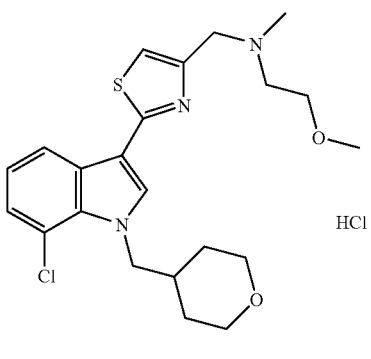 | 8.2 |

TABLE 1-continued

| Example | Chemical name | Chemical structure | pEC$_{50}$ |
|---|---|---|---|
| 32 | 1-(Cyclohexyl)methyl-3-{2-[(diethylamino)methyl]-[1,3]-oxazol-5-yl}-7-methoxy-1H-indole, hydrochloride salt | 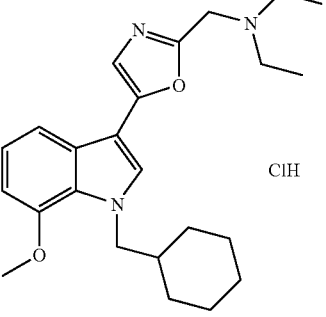 | 7.3 |
| 33 | 1-(Cyclohexyl)methyl-3-(5-ethyl-5,6-dihydro-4H-pyrrolo[3,4-d]isothiazol-3-yl)-7-methoxy-1H-indole, hydrochloride salt | 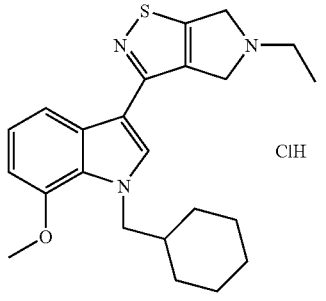 | 7.1 |
| 38 | 1-(Cyclohexyl)methyl-7-methoxy-3-{5-[(pyrrolidin-1-yl)methyl]-[1,3,4]-thiadiazol-2-yl}-1H-indole, hydrochloride salt | 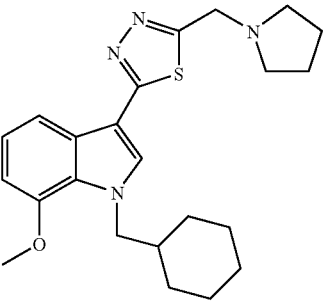 | 7.1 |
| 39 | 7-Chloro-3-{5-[(2,2-dimethyl-pyrolidin-1-yl)methyl]-[1,2,4]oxadiazol-3-yl}-1-(tetrahydropyran-4-yl)methyl-1H-indole, hydrochloride salt | 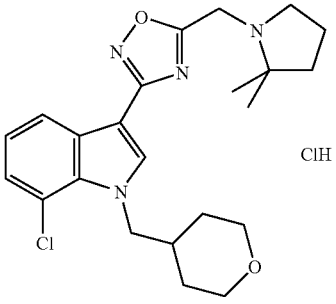 | 7.5 |

EXAMPLE 42

Tail Flick Latency in Mice

Mice were trained to sit still in a tail flick apparatus (Ugo Basile, Italy) whilst tail flick latency was measured. The tail was exposed to a focused beam of radiant heat at a point approximately 2.5 cm from the tip. Tail flick latency was defined as the interval between the appliance of the thermal stimulus and withdrawal of the tail. A 12 second cut-off was employed to prevent tissue damage. Four groups of eight mice were treated with vehicle or one of three doses of the test compound, administered intravenously (vehicle: 10% Tween-80 in saline; injection volume 10 ml/kg). Tail flick latency was measured before administration of the test compound and at regular intervals (typically 20, 40 and 60 minutes) after compound administration. The $ED_{50}$ was calculated at $T_{max}$.

The compounds of examples 2G, 13, 14B, 15A, 15B, 15C, 20, 23B, 23C, 23D and 39 significantly increased the tail flick latency with an $ED_{50}$<5 μmol/kg.

The invention claimed is:
1. An (indol-3-yl)-heterocycle having the general Formula I

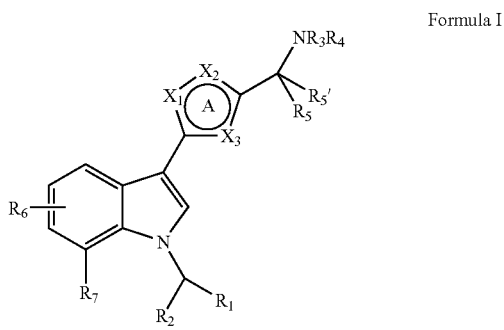

Formula I wherein
A represents a 5-membered aromatic heterocyclic ring, wherein $X_1$, $X_2$ and $X_3$ are independently selected from N, O, S and CR;
R is H or $(C_{1-4})$alkyl;
$R_1$ is cyclohexyl or tetrahydropyranyl;
$R_2$ is H, $CH_3$ or $CH_2$—$CH_3$;
$R_3$ and $R_4$ are independently H or $(C_{1-6})$alkyl the alkyl groups being optionally substituted with OH, $(C_{1-4})$alkyloxy, $(C_{1-4})$alkylthio, $(C_{1-4})$alkylsulfonyl, CN or halogen; or
$R_3$ together with $R_4$ and the N to which they are bonded form piperidine, pyrrolidine, morpholine or thiomorpholine, optionally substituted with OH, $(C_{1-4})$alkyl, $(C_{1-4})$alkyloxy, $(C_{1-4})$alkyloxy-$(C_{1-4})$alkyl, or halogen; or
$R_3$ together with $R_5$ forms a 4-8 membered ring optionally containing a further heteroatom selected from O and S, and which is optionally substituted with OH, $(C_{1-4})$alkyl, $(C_{1-4})$alkyloxy, $(C_{1-4})$alkyloxy-$(C_{1-4})$alkyl, or halogen; or
$R_5$ is H or $(C_{1-4})$alkyl; or
$R_5$ together with $R_3$ forms a 4-8 membered ring optionally containing a further heteroatom selected from O and S, and which is optionally substituted with OH, $(C_{1-4})$alkyl, $(C_{1-4})$alkyloxy, $(C_{1-4})$alkyloxy-$(C_{1-4})$alkyl, or halogen;
$R_5'$ is H or $(C_{1-4})$alkyl;
$R_6$ represents 1-3 substituents independently selected from H, $(C_{1-4})$alkyl, $(C_{1-4})$alkyloxy, CN and halogen;
$R_7$ is H, $(C_{1-4})$alkyl, $(C_{1-4})$alkyloxy, CN or halogen; or
or a pharmaceutically acceptable salt thereof.
2. The (indol-3-yl)-heterocycle of claim 1, wherein $R_2$ is H.
3. The (indol-3-yl)-heterocycle of claim 1, wherein R, $R_5$, $R_5'$ and $R_6$ are H.
4. The (indol-3-yl)-heterocycle of claim 1 where the heterocycle A is 1,2,4-oxadiazole ($X_1$ is N, $X_2$ is O, $X_3$ is N), 1,2,4-thiadiazole ($X_1$ is N, $X_2$ is S, $X_3$ is N) or thiazole ($X_1$ is S, $X_2$ is CR, $X_3$ is N).
5. The (indol-3-yl)-heterocycle of claim 1 which is selected from:
7-Chloro-3-(5-{[N-ethyl-N-(2-methoxyethyl)amino]methyl}-[1,2,4]-thiadiazol-3-yl)-1-(tetrahydropyran-4-yl)methyl-1H-indole;
7-Chloro-3-{5-[(pyrrolidin-1-yl)methyl]-[1,2,4]-thiadiazol-3-yl}-1-(tetrahydropyran-4-yl)methyl-1H-indole;
7-Chloro-3-(5-{[N-ethyl-N-(2-hydroxyethyl)amino]methyl}-[1,2,4]-thiadiazol-3-yl)-1-(tetrahydropyran-4-yl)methyl-1H-indole;
7-Chloro-3-(4-{[N-(2-hydroxyethyl)-N-isopropylamino]methyl}-[1,3]-thiazol-2-yl)-1-(tetrahydropyran-4-yl)methyl-1H-indole;
7-Chloro-3-(4-{[N-ethyl-N-(2-hydroxyethyl)amino]methyl}-[1,3]-thiazol-2-yl)-1-(tetrahydropyran-4-yl)methyl-1H-indole;
7-Chloro-3-(4-{[N-(2-methoxyethyl)-N-methylamino]methyl}-[1,3]-thiazol-2-yl)-1-(tetrahydropyran-4-yl)methyl-1H-indole; and
7-Chloro-3-{5-[(2,2-dimethyl-pyrrolidin-1-yl)methyl]-[1,2,4]oxadiazol-3-yl}-1-(tetrahydropyran-4-yl)methyl-1H-indole;
or a pharmaceutically acceptable salt thereof.
6. A pharmaceutical composition comprising an (indol-3-yl)-heterocycle of claim 1 or a pharmaceutically acceptable salt thereof in admixture with pharmaceutically acceptable auxiliaries.
7. A method of treatment of pain selected from the group consisting of peri-operative pain, chronic pain, neuropathic pain, cancer pain and pain and spasticity associated with multiple sclerosis, the method comprising: administering to a patient in need thereof a therapeutically effective amount of an (indol-3-yl)-heterocycle derivative of claim 1.
8. A pharmaceutical composition comprising an (indol-3-yl)-heterocycle of claim 4 or a pharmaceutically acceptable salt thereof in admixture with pharmaceutically acceptable auxiliaries.
9. A pharmaceutical composition comprising an (indol-3-yl)-heterocycle of claim 5 or a pharmaceutically acceptable salt thereof in admixture with pharmaceutically acceptable auxiliaries.
10. A method of treatment of pain selected from the group consisting of peri-operative pain, chronic pain, neuropathic pain, cancer pain and pain and spasticity associated with multiple sclerosis, the method comprising: administering to a patient in need thereof a therapeutically effective amount of an (indol-3-yl)-heterocycle derivative of claim 4.
11. A method of treatment of pain selected from the group consisting of peri-operative pain, chronic pain, neuropathic pain, cancer pain and pain and spasticity associated with multiple sclerosis, the method comprising: administering to a patient in need thereof a therapeutically effective amount of an (indol-3-yl)-heterocycle derivative of claim 5.

12. The compound of claim 5, wherein the compound is 7-Chloro-3-(4-{[N-(2-hydroxyethyl)-N-isopropylamino]methyl}-[1,3]-thiazol-2-yl)-1-(tetrahydropyran-4-yl)methyl-1H-indole or a pharmaceutically acceptable salt thereof.

13. A pharmaceutical composition comprising the compound or a pharmaceutically acceptable salt thereof of claim 12 in admixture with pharmaceutically acceptable auxiliaries.

14. A method of treatment of pain selected from the group consisting of peri-operative pain, chronic pain, neuropathic pain, cancer pain and pain and spasticity associated with multiple sclerosis, the method comprising: administering to a patient in need thereof a therapeutically effective amount of an (indol-3-yl)-heterocycle derivative of claim 12.

* * * * *